United States Patent [19]
Hillman et al.

[11] Patent Number: 5,843,668
[45] Date of Patent: Dec. 1, 1998

[54] HUMAN SQM1 PROTEIN HOMOLOG

[75] Inventors: Jennifer L. Hillman, San Jose; Surya K. Goli, Sunnyvale, both of Calif.

[73] Assignee: Incyte Pharmaceuticals, Inc., Palo Alto, Calif.

[21] Appl. No.: 757,036

[22] Filed: Nov. 26, 1996

[51] Int. Cl.$^6$ .............................. C12Q 1/68; C12P 19/34; C07H 21/02; C07H 21/04
[52] U.S. Cl. ............................ 435/6; 435/912; 436/94; 536/22.1; 536/23.1; 536/24.3; 536/24.31; 536/24.32; 536/24.33; 536/24.5
[58] Field of Search ........................ 435/6, 91.2; 436/94; 536/22.1, 23.1, 24.3, 24.31, 24.32, 24.33, 24.5; 935/77, 78

[56] References Cited

PUBLICATIONS

Boehim, Klaus, et al., "SQM1 Antibody Defines a Surface Membrane Antigen in Squamous Carcinoma of the Head and Neck," *J. Cancer:*36, 1985, pp. 137–142.

Sambrook et al, "Molecular Cloning: A Laboratory Manual", Cold Spring Harbor Laboratory Press, Cold Spring Harbor, New York, pp. 9.31, 17.2, 1989.

Nicolson, G., "Organ specificity of tumor metastasis: role of preferential adhesion, invasion and growth of malignant cells at specific secondary sites," *Cancer and Metastasis Reviews,* 7:143–188 (1988).

Edelman, G., "Cell Adhesion Molecules in the Regulation of Animal Form and Tissue Pattern," *Ann. Rev. Cell Biol.,* 2:81–116 (1986).

Stoolman, L., "Adhesion Molecules Controlling Lymphocyte Migration," *Cell,* 56:907–910 (1989).

Hynes, R., "Integrins: A Family of Cell Surface Receptors," *Cell,* 48:549–554 (1987).

Wong, Y., et al., "cDNA Cloning of a Novel Cell Adhesion Protein Expressed in Human Squamous Carcinoma Cells," *Biochemical and Biophysical Research Communications,* 166(2) :984–992 (1990) (GI 180233).

Walker, J., et al., "Sequences of 20 Subunits of NADH: Ubiquinone Oxidoreductase from Bovine Heart Mitochondria," *J. Mol. Biol.,* 226:1051–1072 (1992) (GI 244).

Bernal, S., et al., "Congruence of SQM1 Protein Expression with Methotrexate Sensitivity and Transport," *Cancer Investigation,* 13 (1) 23–30 (1995).

Towler, D., et al., "Myristoyl CoA:Protein N–Myristoyltransferase Activities from Rat Liver and Yeast Possess Overlapping Yet Distinct Peptide Substrate Specificites," *The Journal of Biological Chemistry,* 263(4) :1784–1790 (1988).

Kulaylat, M., et al., "Squamoud Cell Carcinoma Complicating Idiopathic Inflammatory Bowel Disease," *Journal of Surgical Oncology,* 59:48–55 (1995).

Vraux, H., et al., "Primary squamous–cell carcinoma of the colon: a case report," *Acta Chir. Belg.,* 94:318–320 (1994).

Rosado–de–Christenson, M., et al., "From the Archives of the AFIP," *Radiographics,* 14(2) :429–446 (1994).

Keita, O., et al., "Primary Bronchogenic Squamous Cell Carcinoma in Children: Report of a Case and Review of the Literature," *Medical and Pediatric Oncology,* 24:50–52 (1995).

Stamenkovic, I., et al., "A Lymphocyte Molecule Implicated in Lymph Node Homing is a Member of the Cartilage Link Protein Family," *Cell,* 56:1057–1062 (1989).

*Primary Examiner*—W. Gary Jones
*Assistant Examiner*—Jeffrey Fredman
*Attorney, Agent, or Firm*—Sheela Mohan-Peterson; Lucy J. Billings; Incyte Pharmaceuticals, Inc.

[57] ABSTRACT

The present invention provides a polynucleotide which identifies and encodes a novel human SQM2. The invention provides for genetically engineered expression vectors and host cells comprising the nucleic acid sequence encoding human SQM2. The invention also provides for the use of purified SQM2 and its agonists in the production of recombinant proteins and in pharmaceutical compositions for the treatment of diseases associated with the expression of SQM2. Additionally, the invention provides for the use of SQM2 antagonists and inhibitors, including antisense molecules to SQM2 polynucleotides (i.e., gene sequences) in pharmaceutical compositions for the treatment of diseases associated with the expression of SQM2. The invention also describes diagnostic assays which utilize the polynucleotide to hybridize with the transcripts and/or genomic DNA encoding SQM2 and anti-human SQM2 antibodies which specifically bind to SQM2.

12 Claims, 5 Drawing Sheets

```
                 9              18              27              36              45              54
5' GTT CCG GGT AGG AGC TAG GTG ACC CTC GGC TGC TGC AGG GAT CTG CAG CGG ACT 63              72              81              90              99             108
    GCA GCC ATG GGG GCG CAC CTG GTC CGG CGC TAC CTG GGC GAT GCC TCG GTG GAG
            M   G   A   H   L   V   R   R   Y   L   G   D   A   S   V   E 117             126             135             144             153             162
    CCC GAC CCC CTG CAG ATG CCA ACC TTC CCG CCA KAC TAC GGC TTC CCC GAA CGC
     P   D   P   L   Q   M   P   T   F   P   P   X   Y   G   F   P   E   R 171             180             189             198             207             216
    AAG GAG CGC GAG ATG GTG GCC ACA MAG CAG GAK ATG ATG GGA CGC GCA CYT GAG
     K   E   R   E   M   V   A   T   X   Q   X   M   M   G   R   A   X   E 225             234             243             252             261             270
    GCT CCA GCT GTC GGG GAC TAC TGC GCC CAC CAC CTC ATC CGG CTG CTC AAG TGC
     A   P   A   V   G   D   Y   C   A   H   H   L   I   R   L   L   K   C 279             288             297             306             315             324
    AAG CGT GAC AGC TTC CCC AAC TTC CTG GCC TGC AAG CAG GAG CGG CAC GAC TGG
     K   R   D   S   F   P   N   F   L   A   C   K   Q   E   R   H   D   W 333             342             351             360             369             378
    GAC TAC TGC GAG CAC CGC GAC TAT GTG ATG CGC ATG AAG GAG TTT GAG CGG GAG
     D   Y   C   E   H   R   D   Y   V   M   R   M   K   E   F   E   R   E 387             396             405             414             423             432
    CGG AGG CTG CTC CAG CGG AAG AAG CGG CGG GAG AAG AAG GCG GCA GAG TTG GCC
     R   R   L   L   Q   R   K   K   R   R   E   K   K   A   A   E   L   A 441             450             459             468             477             486
    AAA GGC CAG GGA CCC GGG GAA GTG GAC CCC AAG GTG GCC CTG TAG GGG GTG CAC
     K   G   Q   G   P   G   E   V   D   P   K   V   A   L 495             504             513             522
    CCC CCA CCC TAT GGA CCA GTC AAA TAA AAG CCT TCA GGC CCC TC 3'
```

FIGURE 1

```
  1  MGAHLVRRYLGDASVEPDDPLQMPTFPPP X YGFPERKEREMV      698022
  1  MGAHLVRRYLGDASVEPDDPLQMPTFPPP D YGFPERKEREMV      GI 180233
  1  MGAHL A RRYLGDASVEPDDPL R MPTFPPP D YGFPERKEREMV  GI 244

41  AT X Q X MMGRA X EAPAVGDYCAHHLIRLLKCKRDSFPNFLA    698022
 41  AT Q Q E MM D A--SEAQLRDYCAHHLIRLLKCKRDSFP SCWP   GI 180233
 41  AT Q Q E MN DAQLVLQQR-IDYCAH Y LIR F LKCKRDSFPNFLA GI 244

81  CKQERHDWDYCEHRDYVMRMKEFERRLL QRKKKRREKKA         698022
 79  ASR K RHDSGLLRTAS YVMRMKEFERDEGC-SSGRSGGRRR      GI 180233
 80  CK H ERHDWDYCEH L DYV K RMKEFERERRLLQRKKKRRE QRE GI 244

121  AELAKGQQGPGEVDPKVAL                              698022
118  RQIC KGQ GPGEVDPKVAL                             GI 180233
120  AD M AKGL L GPGEVA P EVAL                        GI 244
```

FIGURE 2

| Library | Lib Description | Abun | Pct Abun |
|---|---|---|---|
| COLNNOT05 | colon, 40 M, match to COLNCRT01 | 2 | 0.0577 |
| SYNORAT03 | synovium, wrist, rheumatoid, 56 F | 1 | 0.0169 |
| BRSTNOT03 | breast, 54 F, match to BRSTTUT02 | 1 | 0.0146 |

FIGURE 3

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 138 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: synorat03
        ( B ) CLONE: 698022

( x i ) SEQUENCE DESCRIPTION: SEQ ID NO:1:

```
Met Gly Ala His Leu Val Arg Arg Tyr Leu Gly Asp Ala Ser Val Glu
  1               5                  10                  15

Pro Asp Pro Leu Gln Met Pro Thr Phe Pro Pro Xaa Tyr Gly Phe Pro
             20                  25                  30

Glu Arg Lys Glu Arg Glu Met Val Ala Thr Xaa Gln Xaa Met Met Gly
         35                  40                  45

Arg Ala Xaa Glu Ala Pro Ala Val Gly Asp Tyr Cys Ala His His Leu
     50                  55                  60

Ile Arg Leu Leu Lys Cys Lys Arg Asp Ser Phe Pro Asn Phe Leu Ala
 65                  70                  75                  80

Cys Lys Gln Glu Arg His Asp Trp Asp Tyr Cys Glu His Arg Asp Tyr
                 85                  90                  95
```

| Val | Met | Arg | Met<br>100 | Lys | Glu | Phe | Glu | Arg<br>105 | Glu | Arg | Arg | Leu | Leu<br>110 | Gln | Arg |
| --- | --- | --- | --- | --- | --- | --- | --- | --- | --- | --- | --- | --- | --- | --- | --- |
| Lys | Lys | Arg<br>115 | Arg | Glu | Lys | Lys | Ala<br>120 | Ala | Glu | Leu | Ala | Lys<br>125 | Gly | Gln | Gly |
| Pro | Gly<br>130 | Glu | Val | Asp | Pro | Lys<br>135 | Val | Ala | Leu | | | | | | |

( 2 ) INFORMATION FOR SEQ ID NO:2:

( i ) SEQUENCE CHARACTERISTICS:
        ( A ) LENGTH: 530 base pairs
        ( B ) TYPE: nucleic acid
        ( C ) STRANDEDNESS: single
        ( D ) TOPOLOGY: linear ( v i i ) IMMEDIATE SOURCE:
        ( A ) LIBRARY: synorat03
        ( B ) CLONE: 698022

( x i ) SEQUENCE DESCRIPTION: SEQ ID NO:2:

```
GTTCCGGGTA GGAGCTAGGT GACCCTCGGC TGCTGCAGGG ATCTGCAGCG GACTGCAGCC      60
ATGGGGGCGC ACCTGGTCCG GCGCTACCTG GGCGATGCCT CGGTGGAGCC CGACCCCCTG     120
CAGATGCCAA CCTTCCCGCC AKACTACGGC TTCCCCGAAC GCAAGGAGCG CGAGATGGTG     180
GCCACAMAGC AGGAKATGAT GGGACGCGCA CYTGAGGCTC CAGCTGTCGG GGACTACTGC     240
GCCCACCACC TCATCCGGCT GCTCAAGTGC AAGCGTGACA GCTTCCCCAA CTTCCTGGCC     300
TGCAAGCAGG AGCGGCACGA CTGGGACTAC TGCGAGCACC GCGACTATGT GATGCGCATG     360
AAGGAGTTTG AGCGGGAGCG GAGGCTGCTC CAGCGGAAGA AGCGGCGGGA GAAGAAGGCG     420
GCAGAGTTGG CCAAAGGCCA GGGACCCGGG GAAGTGGACC CCAAGGTGGC CCTGTAGGGG     480
GTGCACCCCC CACCCTATGG ACCAGTCAAA TAAAAGCCTT CAGGCCCCTC                530
```

( 2 ) INFORMATION FOR SEQ ID NO:3:

( i ) SEQUENCE CHARACTERISTICS:
        ( A ) LENGTH: 135 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: GenBank
        ( B ) CLONE: 180233

( x i ) SEQUENCE DESCRIPTION: SEQ ID NO:3:

| Met<br>1 | Gly | Ala | His | Leu<br>5 | Val | Arg | Arg | Tyr | Leu<br>10 | Gly | Asp | Ala | Ser | Val<br>15 | Glu |
| --- | --- | --- | --- | --- | --- | --- | --- | --- | --- | --- | --- | --- | --- | --- | --- |
| Pro | Asp | Pro | Leu<br>20 | Gln | Met | Pro | Thr | Phe<br>25 | Pro | Pro | Asp | Tyr | Gly<br>30 | Phe | Pro |
| Glu | Arg | Lys<br>35 | Glu | Arg | Glu | Met | Val<br>40 | Ala | Thr | Gln | Gln | Glu<br>45 | Met | Met | Asp |
| Ala | Ser<br>50 | Glu | Ala | Gln | Leu | Arg<br>55 | Asp | Tyr | Cys | Ala | His<br>60 | His | Leu | Ile | Arg |
| Leu<br>65 | Leu | Lys | Cys | Lys | Arg<br>70 | Asp | Ser | Phe | Pro | Ser<br>75 | Cys | Trp | Pro | Ala | Ser<br>80 |
| Arg | Lys | Arg | His | Asp<br>85 | Ser | Gly | Leu | Leu | Arg<br>90 | Thr | Ala | Ser | Tyr | Val<br>95 | Met |
| Arg | Met | Lys | Glu<br>100 | Phe | Glu | Arg | Asp | Glu<br>105 | Gly | Cys | Ser | Ser | Gly<br>110 | Arg | Ser |

-continued

| Gly | Gly | Arg | Arg | Arg | Arg | Gln | Ile | Cys | Lys | Gly | Gln | Gly | Pro | Gly | Glu |
|---|---|---|---|---|---|---|---|---|---|---|---|---|---|---|---|
| | | 115 | | | | | 120 | | | | | 125 | | | |

| Val | Asp | Pro | Lys | Val | Ala | Leu |
|---|---|---|---|---|---|---|
| | 130 | | | | | 135 |

(2) INFORMATION FOR SEQ ID NO:4:

(i) SEQUENCE CHARACTERISTICS:
        (A) LENGTH: 137 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 244

(xi) SEQUENCE DESCRIPTION: SEQ ID NO:4:

| Met | Gly | Ala | His | Leu | Ala | Arg | Arg | Tyr | Leu | Gly | Asp | Ala | Ser | Val | Glu |
|---|---|---|---|---|---|---|---|---|---|---|---|---|---|---|---|
| 1 | | | | 5 | | | | | 10 | | | | | 15 | |

| Pro | Asp | Pro | Leu | Arg | Met | Pro | Thr | Phe | Pro | Pro | Asp | Tyr | Gly | Phe | Pro |
|---|---|---|---|---|---|---|---|---|---|---|---|---|---|---|---|
| | | | 20 | | | | | 25 | | | | | 30 | | |

| Glu | Arg | Lys | Glu | Arg | Glu | Met | Val | Ala | Thr | Gln | Gln | Glu | Met | Asn | Asp |
|---|---|---|---|---|---|---|---|---|---|---|---|---|---|---|---|
| | | 35 | | | | | 40 | | | | | 45 | | | |

| Ala | Gln | Leu | Val | Leu | Gln | Gln | Arg | Asp | Tyr | Cys | Ala | His | Tyr | Leu | Ile |
|---|---|---|---|---|---|---|---|---|---|---|---|---|---|---|---|
| | 50 | | | | | 55 | | | | | | 60 | | | |

| Arg | Phe | Leu | Lys | Cys | Lys | Arg | Asp | Ser | Phe | Pro | Asn | Phe | Leu | Ala | Cys |
|---|---|---|---|---|---|---|---|---|---|---|---|---|---|---|---|
| 65 | | | | | 70 | | | | | 75 | | | | | 80 |

| Lys | His | Glu | Arg | His | Asp | Trp | Asp | Tyr | Cys | Glu | His | Leu | Asp | Tyr | Val |
|---|---|---|---|---|---|---|---|---|---|---|---|---|---|---|---|
| | | | | 85 | | | | | 90 | | | | | 95 | |

| Lys | Arg | Met | Lys | Glu | Phe | Glu | Arg | Glu | Arg | Arg | Leu | Leu | Gln | Arg | Lys |
|---|---|---|---|---|---|---|---|---|---|---|---|---|---|---|---|
| | | | 100 | | | | | 105 | | | | | 110 | | |

| Lys | Arg | Arg | Glu | Gln | Arg | Glu | Ala | Asp | Met | Ala | Lys | Gly | Leu | Gly | Pro |
|---|---|---|---|---|---|---|---|---|---|---|---|---|---|---|---|
| | | 115 | | | | | 120 | | | | | 125 | | | |

| Gly | Glu | Val | Ala | Pro | Glu | Val | Ala | Leu |
|---|---|---|---|---|---|---|---|---|
| | 130 | | | | | 135 | | |

HUMAN SQM1 PROTEIN HOMOLOG

FIELD OF THE INVENTION

The present invention relates to nucleic acid and amino acid sequences of a novel human SQM1 protein homolog, SQM2, which comprises a cell adhesion protein. The novel human SQM2 protein shares features with other human cell adhesion proteins including the human SQM1 protein, a cell adhesion protein expressed in human squamous carcinoma cells. The present invention relates to the use of these novel sequences in the diagnosis, prevention and treatment of disease.

BACKGROUND OF THE INVENTION

Cell adhesion molecules are cell surface proteins involved in the recognition and adhesion of one cell to another as well as adhesion of cells to substrates. Such cell-cell and cell-substrate interactions are essential for the correct assembly of tissues during development. In addition to playing a role in development, cell adhesion molecules are involved in tumor growth and metastasis, cellular differentiation, immunological response, wound healing and coagulation [Nicolson (1988) Cancer Metastasis Rev. 7:143; Edelman (1986) Annu. Rev. Cell. Biol. 2:81; and Stoolman (1989) Cell 56:907].

Cell adhesion molecules (CAMs) act as molecular recognition systems which allow cells to interact in specific ways with similar and dissimilar cell types. Cell adhesion molecules include the integrins (e.g., LFA-1, Mac-1, the VLA antigens), the selecting, cadherins (e.g., N-cadherin, E-cadherin and P-cadherin) and members of the immunoglobulin superfamily (e.g., CD2, LPA-3, ICAM-1, ICAM-2, N-CAM, and VCAM-1).

The integrins are a diverse group of transmembrane glycoproteins which comprise heterodimers containing an α and a β subunit [Hynes (1987) Cell 48:549]. Integrins are involved in cell-cell interactions (e.g., during T lymphocyte help), interactions with extracellular matrix glycoproteins (e.g., fibronectin, vitronectin, laminin), binding to complement components and coagulation factors.

The selectins comprise a family of CAMs found on the surface of leukocytes, platelets and endothelial cells. Selectins include the lymphocyte homing receptors (e.g., Mel-14), the human endothelial leukocyte adhesion molecule ELAM-1 and the Hermes/CD44 family whose members have been implicated in lymphocyte-endothelial cell adhesion in a variety of tissues [Stoolman (1989) Cell 56:907]. Selectins mediate interactions between leukocytes and endothelium during lymphocyte recirculation, coagulation and inflammation.

CAMs in the immunoglobulin superfamily, such as N-CAM and L-CAM, have been shown to be important in morphogenesis during the development of embryos [Edelman (1986) Annu. Rev. Cell Biol. 2:81].

Cell adhesion molecules located on the surface of epithelial cells have been identified and include the SQM1 protein [Wong et al. (1990) Biochem. Biophys. Res. Comm. 166:984]. Sequence analysis of the human SQM1 gene has revealed that SQM1 is distinct yet related to the β subunit of integrins. SQM1 is related to the β subunit of the human leukocyte adhesion proteins [Wong et al. (1990), supra] and is also related to the B18 subunit of the bovine NADH:ubiquinone oxidoreductase [Walker et al. (1992) J. Mol. Biol. 226:1051].

SQM1 is found on human squamous epithelial cells, including squamous carcinoma cells, and has been shown to be involved in cell adhesion of squamous epithelial cells, endothelial cells and extracellular matrix proteins. Antibodies directed against SQM1 preferentially inhibit adhesion interactions between epithelial and endothelial cells and between epithelial cells and extracellular matrix proteins (e.g., fibronectin and collagen) [Wong et al. (1990), supra]. This data supports a role for SQM1 in the metastasis of epithelial tumors. It has been proposed that SQM1-expressing squamous carcinoma cells which detach from the primary tumor site are capable of adhering to and penetrating the subendothelial matrix and endothelium to establish secondary tumor sites [Wong et al. (1990), supra].

In addition to its role in cell adhesion and tumor metastasis, a reduction in the expression of SQM1 has been shown to closely correlate with the development of resistance to methotrexate (MTX) in human squamous carcinoma of the head and neck cell lines implicating SQM1 in the transport of MTX, a frequently used pharmacological agent [Bernal et al. (1995) Cancer Invest. 13:23].

Because of the important cellular functions of SQM1 that are associated with tumor growth and metastasis it is important to determine whether tumor cells (e.g., from biopsy material) express SQM1 markers (i.e., molecules that are structurally or functionally related to SQM1). Assays are needed for the development of new diagnostic or therapeutic compositions directed at SQM1 markers.

SUMMARY

The present invention discloses a novel human SQM1 protein homolog hereinafter referred to as SQM2, which shares features with the human SQM1 protein, a cell adhesion molecule shown to be related but distinct from the β subunit of integrins. Cell adhesion molecules are known to play an important role in the regulation of cell growth and development, including metastatic potential. Accordingly, the invention provides a substantially purified polypeptide comprising the amino acid sequence of SEQ ID NO:1. In an alternative embodiment, the present invention provides fragments of isolated (i.e., substantially purified) human SQM2 about 6 amino acid residues in length which are unique (i.e., having less than about 25% identity to portions of another protein) to SQM2 (e.g., residues 118–123 of SEQ ID NO:1). In another embodiment, the present invention provides portions (i.e., fragments) of isolated human SQM2 comprising a carboxy-terminal portion of SEQ ID NO:1 having a length greater than 16 amino acid residues; these carboxy-terminal portions comprise a variable region of SQM2 located between residues 118–123 of SEQ ID NO:1.

The present invention further provides an isolated polynucleotide sequence encoding the polypeptide comprising the amino acid sequence of SEQ ID NO:1. In a preferred embodiment, the isolated polynucleotide comprises the nucleic acid sequence of SEQ ID NO:2 or variants thereof; these nucleic acid sequences may comprise the entire nucleic acid sequence of SEQ ID NO:2 or fragments thereof.

In yet another embodiment, the present invention provides polynucleotide sequences comprising the complement of the nucleic acid sequence of SEQ ID NO:2 or variants thereof; these complementary nucleic acid sequences may comprise the complement of the entire nucleic acid sequence of SEQ ID NO:2 or fragments thereof.

In another embodiment, the present invention provides a polynucleotide sequence that hybridizes under stringent conditions to the nucleic acid sequence of SEQ ID NO:2. The invention further relates to the nucleic acid sequence encoding human SQM2, oligonucleotides, peptide nucleic acids (PNA), fragments, portions or antisense molecules thereof.

The present invention also provides a method for detecting the presence of polynucleotide sequences encoding at least a portion of human SQM2 in a biological sample, comprising the steps of: a) providing: i) a biological sample suspected of containing nucleic acid corresponding to the polynucleotide sequence of SEQ ID NO:2; ii) the polynucleotide of SEQ ID NO:2, or a fragment thereof; b) combining the biological sample with the polynucleotide under conditions such that a hybridization complex is formed between the nucleic acid and the polynucleotide; and c) detecting the hybridization complex. The method of the present invention is not limited by the nature of the nucleic acid corresponding to the polynucleotide sequence of SEQ ID NO:2. In a preferred embodiment, the nucleic acid is ribonucleic acid (RNA) and the detection of a hybridization complex between SEQ ID NO:2 and the RNA correlates with expression of the polynucleotide of SEQ ID NO:2 in the biological sample. In another preferred embodiment, the nucleic acid corresponding to the polynucleotide sequence of SEQ ID NO:2 is deoxyribonucleic acid (DNA) and the detection of a hybridization complex between the DNA in a sample and SEQ ID NO:2 is performed under conditions that permit the detection of alterations (e.g., deletions, translocations, insertions, point mutations, etc.) in the polynucleotide of SEQ ID NO:2 in the biological sample.

The present invention further provides an antisense molecule comprising the nucleic acid sequence complementary to at least a portion of the polynucleotide of SEQ ID NO:2. In another embodiment, the present invention provides a pharmaceutical composition comprising an antisense molecule comprising the nucleic acid sequence complementary to at least a portion of the polynucleotide of SEQ ID NO:2 and a pharmaceutically acceptable excipient. Delivery of pharmaceutical compositions comprising SQM2 nucleic acids (sense and anti-sense) may be accomplished using a variety of methods known to the art including the use of liposomes. The present invention contemplates pharmaceutical compositions comprising SQM2 nucleic acids (sense and anti-sense) in a liposome.

In another embodiment, the present invention provides an isolated polynucleotide comprising at least a portion of the nucleic acid sequence of SEQ ID NO:2 or variants thereof contained on a recombinant expression vector. In yet another embodiment, the expression vector containing the polynucleotide sequence is contained within a host cell. The invention is not limited by the nature of the host cell employed. For example, the host cell may be an *E. coli* cell, a yeast cell, an insect cell, a mammalian cell, etc.

The present invention further provides a method for producing a polypeptide comprising the amino acid sequence of SEQ ID NO:1, the method comprising the steps of: a) culturing the host cell containing an expression vector containing an isolated polynucleotide comprising the nucleic acid sequence of SEQ ID NO:2 or variants thereof under conditions suitable for the expression of the polypeptide; and b) recovering the polypeptide from the host cell culture.

The present invention still further provides a method for producing a polypeptide comprising the amino acid sequence of SEQ ID NO:1, the method comprising the steps of: a) culturing the host cell containing an expression vector containing an isolated polynucleotide comprising at least a portion of the nucleic acid sequence of SEQ ID NO:2 or variants thereof, said portion comprising a nucleotide sequence encoding a variable region of SQM2 (i.e., SEQ ID NO:1), under conditions suitable for the expression of the polypeptide; and b) recovering the polypeptide from the host cell culture.

In another embodiment, the present invention provides a pharmaceutical composition comprising a substantially purified polypeptide comprising the amino acid sequence of SEQ ID NO:1 and a pharmaceutically acceptable excipient. In yet another embodiment, the present invention provides a pharmaceutical composition comprising a substantially purified polypeptide comprising a carboxy-terminal portion of SEQ ID NO:1 having a length greater then 16 amino acids and a pharmaceutically acceptable excipient.

The present invention also provides a purified antibody which binds specifically to a polypeptide comprising at least a portion of the amino acid sequence of SEQ ID NO:1, said portion comprising a variable region of SEQ ID NO:1. The present invention further provides a pharmaceutical composition comprising a purified antibody which binds specifically to a polypeptide comprising at least a portion of the amino acid sequence of SEQ ID NO:1, said portion comprising a variable region of SEQ ID NO:1, and a pharmaceutically acceptable excipient.

The present invention also provides a method for detecting the expression of human SQM2 in a biological sample comprising the steps of: a) providing: i) a biological sample suspected of expressing human SQM2 protein; and ii) a purified antibody which binds specifically to a polypeptide comprising at least a portion of the amino acid sequence of SEQ ID NO:1, said portion comprising a variable region of SEQ ID NO:1; b) combining the biological sample and the antibody under conditions such that an antibody:protein complex is formed; and c) detecting the complex wherein the presence of the complex correlates with the expression of the protein in the biological sample.

BRIEF DESCRIPTION OF THE FIGURES

FIG. 1 shows the amino acid sequence (SEQ ID NO:1) and nucleic acid sequence (SEQ ID NO:2) of human SQM2. The alignment was produced using MACDNASIS™ software (Hitachi Software Engineering Co. Ltd., Yokohama, Japan).

FIG. 2 shows the amino acid sequence alignment between human SQM2 (698022; SEQ ID NO:1), human SQM1 [GI 180233 (SEQ ID NO:3); Wong et al. (1990), supra], and the B 18 subunit of the bovine NADH:ubiquinone oxidoreductase [GI 244 (SEQ ID NO:4); Walker et al. (1992), supra]. This alignment were produced using the multisequence alignment program of DNASTAR™ software (DNAStar Inc., Madison, Wis.).

FIG. 3 shows the northern analysis for Incyte Clone 698022 (SEQ ID NO:2). The northern analysis was produced electronically using the LIFESEQ® database (Incyte Pharmaceuticals, Palo Alto, Calif.) and shows cDNA libraries in which sequences encoding human SQM2 were expressed.

DEFINITIONS

Figure 4:
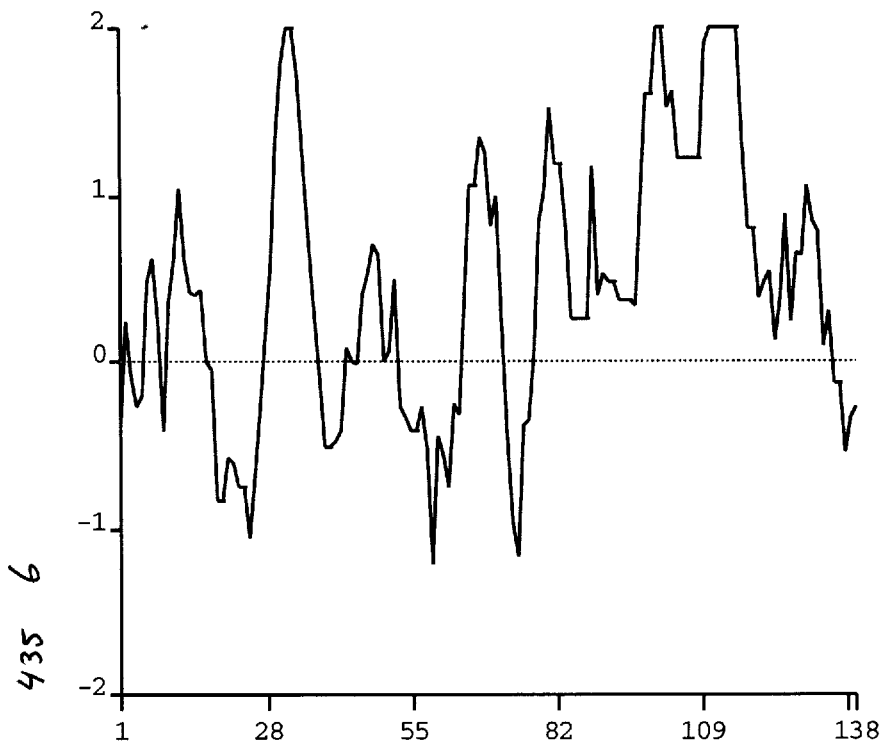
FIGS. 4A and 4B show the hydrophobicity plot for human SQM2 (SEQ ID NO:1) and SQM1 (SEQ ID NO:3), respectively. These plots were generated using MACDNASIS™ software; the X axis reflects amino acid position, and the negative Y axis, hydrophobicity.
Figure 4:
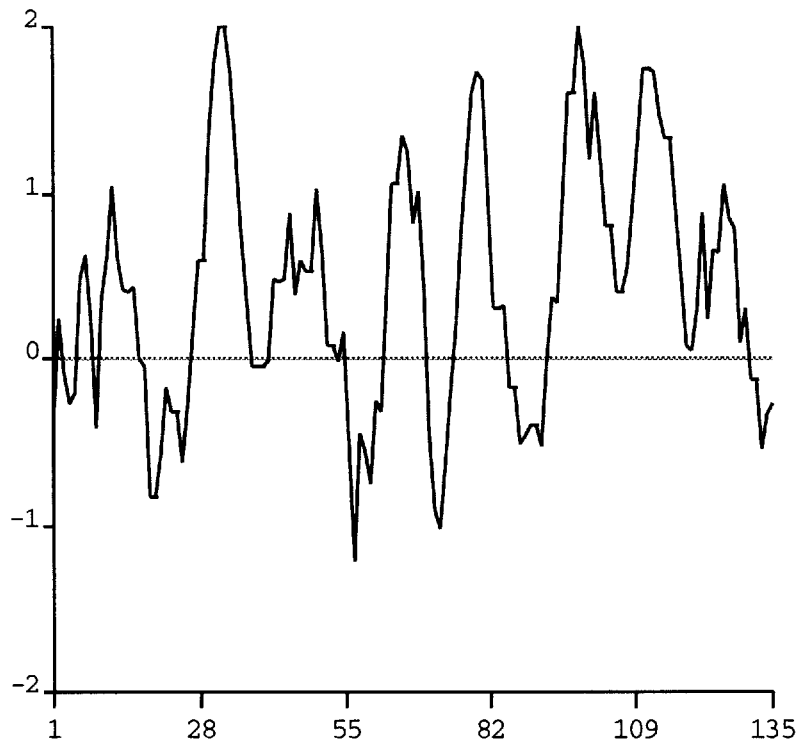

To facilitate understanding of the invention, a number of terms are defined below.

"SQM1 markers" as used herein refers to molecules which are either structurally related to the human SQM1 protein or which are functionally related to SQM1 (i.e., molecules which provide functions of SQM1, such as cell adhesion, affect MTX transport, etc.).

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, "amino acid sequence" as used herein refers to peptide or protein sequence.

"Peptide nucleic acid" ("PNA") as used herein refers to a molecule which comprises an oligomer to which an amino acid residue, such as lysine, and an amino group have been added. These small molecules, also designated anti-gene agents, stop transcript elongation by binding to their complementary strand of nucleic acid [Nielsen P. E. et al. (1993) Anticancer Drug Des 8:53–63].

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to, for example, the naturally occurring human SQM2.

A "substitution" results from the replacement of one or more nucleotides or amino acids by different nucleotides or amino acids, respectively.

As used herein, "SQM2" refers to the amino acid sequence of substantially purified SQM2 obtained from any species, particularly mammalian, including bovine, ovine, porcine, murine, equine, and preferably human, from any source whether natural, synthetic, semi-synthetic or recombinant.

A "variant" of SQM2 is defined as an amino acid sequence which differs by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions (i.e., additions), or both. Guidance in determining which and how many amino acid residues may be substituted, inserted or deleted without abolishing biological or immunological activity may be found using computer programs well known in the art, for example, DNAStar software.

The term "biologically active" refers to a SQM2 molecule having structural, regulatory or biochemical functions of a naturally occurring SQM2. Likewise, "immunologically active" defines the capability of the natural, recombinant or synthetic SQM2, or any oligopeptide thereof, to induce a specific immune response in appropriate animals or cells and to bind with specific antibodies.

The term "derivative" as used herein refers to the chemical modification of a nucleic acid encoding SQM2 or the encoded SQM2. Illustrative of such modifications would be replacement of hydrogen by an alkyl, acyl, or amino group. A nucleic acid derivative would encode a polypeptide which retains essential biological characteristics of natural human SQM2.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated. An "isolated polynucleotide" is therefore a substantially purified polynucleotide.

"Amplification" is defined as the production of additional copies of a nucleic acid sequence and is generally carried out using polymerase chain reaction technologies well known in the art [Dieffenbach C. W. and G. S. Dveksler (1995) PCR Primer, a Laboratory Manual, Cold Spring Harbor Press, Plainview, N.Y.].

The term "hybridization" as used herein refers to any process by which a strand of nucleic acid joins with a complementary strand through base pairing.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized to a solid support [e.g., a nylon membrane or a nitrocellulose filter as employed in Southern and Northern blotting, dot blotting or a glass slide as employed in in situ hybridization, including FISH (fluorescent in situ hybridization)].

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

Low stringency conditions comprise conditions equivalent to binding or hybridization at 42° C. in a solution consisting of 5× SSPE (43.8 g/l NaCl, 6.9 g/l NaH$_2$PO$_4$.H$_2$O and 1.85 g/l EDTA, pH adjusted to 7.4 with NaOH), 0.1% SDS, 5× Denhardt's reagent [50× Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5× SSPE, 0.1% SDS at 42° C. when a probe of about 500 nucleotides in length is employed.

High stringency conditions comprise conditions equivalent to binding or hybridization at 42° C. in a solution consisting of 5× SSPE (43.8 g/l NaCl, 6.9 g/l NaH$_2$PO$_4$.H$_2$O and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1× SSPE, 1.0% SDS at 42° C. when a probe of about 500 nucleotides in length is employed.

The art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above listed conditions. The term "hybridization" as used herein includes "any process by which a strand of nucleic acid joins with a complementary strand through base pairing" [Coombs J. (1994) *Dictionary of Biotechnology*, Stockton Press, New York, N.Y.].

"Stringency" typically occurs in a range from about $T_m$–5° C. (5° C. below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences. Under "stringent conditions" SEQ ID NO:2 or fragments thereof will hybridize to its exact complement and closely related sequences. The stringent conditions are chosen such that SEQ ID NO:2 or fragments thereof will hybridize to sequences encoding human SQM2 but not to sequences encoding human SQM1 (i.e., SEQ ID NO:5 or its RNA equivalents) or the B18 subunit of the bovine NADH:ubiquinone oxidoreductase (i.e., SEQ ID NO:6 or its RNA equivalents). When fragments of SEQ ID NO:2 are employed in hybridization reactions, the stringent conditions include the choice of fragments of SEQ ID NO:2 to be used. Fragments of SEQ ID NO:2 which contain unique sequences (i.e., regions which are either non-homologous to or which contain less than about 50% homology or complementarity with SEQ ID NOS:5 or 6) are preferentially employed. SEQ ID NOS:5 and 6 represent DNA sequences encoding the human SQM1 and bovine B18 subunit proteins, respectively.

As used herein, the term "antisense" is used in reference to RNA sequences which are complementary to a specific RNA sequence (e.g., mRNA). Antisense RNA may be produced by any method, including synthesis by splicing the gene(s) of interest in a reverse orientation to a viral promoter which permits the synthesis of a coding strand. Once introduced into a cell, this transcribed strand combines with natural mRNA produced by the cell to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (–) (i.e., "negative") is sometimes used in reference to the antisense strand, with the designation (+) sometimes used in reference to the sense (i.e., "positive") strand.

As used herein the term "portion" when in reference to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:2" encompasses the full-length human SQM2 protein and fragments thereof.

A "carboxy-terminal fragment of SQM2" refers to fragments (i.e., portions) of SQM2 (SEQ ID NO:1) which contain the carboxy-terminal residue (i.e., residue 138 of SEQ ID NO:138). For example, a fragment consisting of residues 115–138 of SEQ ID NO:1 is a carboxy-terminal fragment of SQM2.

As used herein the terms "a variable region of SQM2" or "a variable region of SEQ ID NO:1 " refer to regions of SEQ ID NO:1 which are unique (i.e., having less than about 25% identity to portions of another protein) to SQM2. For example, as shown by the alignment provided in FIG. 2, residues 118–123 of SEQ ID NO:1 are unique in comparison to the related but distinct SQM1 (GI 180233) and B18 subunit (GI 244) proteins. This portion of the SQM2 protein therefore comprises a variable region of SQM2.

The term "antigenic determinant" as used herein refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A", the presence of a protein containing epitope A (or free, unlabelled A) in a reaction containing labelled "A" and the antibody will reduce the amount of labelled A bound to the antibody.

The term "sample" as used herein is used in its broadest sense. A biological sample suspected of containing nucleic acid encoding human SQM2 may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

The term "correlates with expression of a polynucleotide" as used herein indicates that the detection of the presence of ribonucleic acid complementary to SEQ ID NO:2 by hybridization assays is indicative of the presence of mRNA encoding human SQM2 in a sample and thereby correlates with expression of the SQM2 mRNA from the gene encoding SQM2.

"Alterations in the polynucleotide of SEQ ID NO:2" as used herein comprise any alteration in the sequence of polynucleotides encoding human SQM2 including deletions, insertions, and point mutations that may be detected using hybridization assays. Included within this definition is the detection of alterations to the genomic DNA sequence which encodes human SQM2 [e.g., by alterations in pattern of restriction enzyme fragments capable of hybridizing to SEQ ID NO:2 (RFLP analysis), the inability of a selected fragment of SEQ ID NO:2 to hybridize to a sample of genomic DNA (e.g., using allele-specific oligonucleotide probes), improper or unexpected hybridization, such as hybridization to a locus other than the normal chromosomal locus for the SQM2 gene (e.g., using FISH to metaphase chromosomes spreads, etc.)].

DESCRIPTION OF THE INVENTION

Given the role cell adhesion molecules play in regulating cell growth and development, the discovery of new cell adhesion molecules is useful for developing diagnostic or therapeutic compositions directed at detecting or preventing neoplasia and/or metastasis. Specifically, the expression of SQM1 markers (i.e., proteins which are either structurally or functionally related to SQM1) may predict the clinical course of neoplastic disease (e.g., metastatic or non-metastatic). Moreover, SQM1 markers may indicate resistance to chemotherapeutic agents. In this regard, reduced expression of the SQM1 cell adhesion molecule is associated with a reduced ability of squamous carcinoma cell lines to transport methotrexate, a compound used frequently for chemotherapy. Thus, novel human SQM1-related genes and proteins (i.e., SQM1 markers) are useful for developing diagnostic or therapeutic compositions directed at detection and treatment of methotrexate-resistance due to reduced methotrexate transport during chemotherapy.

The present invention relates to a novel human SQM1 homolog, SQM2, which was initially identified among the partial cDNAs from a rheumatoid wrist synovium library (SYNORAT03) and to the use of the disclosed nucleic acid and amino acid sequences in the study, diagnosis, prevention and treatment of disease.

The nucleic acid sequence encoding a portion of the novel human SQM2 protein was identified in Incyte Clone 698022 through a computer-generated search for amino acid sequence alignments. The nucleic acid sequence, SEQ ID NO:2, disclosed herein, encodes the amino acid sequence, SEQ ID NO:1, human SQM2 (FIG. 1). The full length cDNA was isolated from first pass cDNA from the SYNORAT03 library and in addition, the full length cDNA was independently assembled from Incyte Clones 113134; 698022; 1269386; and 1379443 from the LIFESEQ® database (Incyte Pharmaceuticals, Palo Alto, Calif.).

The human SQM2 of the present invention is here described as having 138 amino acid residues, a number of which are residues shown to be conserved with the human SQM1 protein (GI 180233; SEQ ID NO:3) and the B18 subunit of bovine NADH:ubiquinone oxidoreductase (GI 244; SEQ ID NO:4) (see alignment provided in FIG. 2). This alignment also shows that portions of SQM2 are unique (e.g., residues 118–123 of SEQ ID NO:1); these unique portions are referred to as variable regions of SQM2. Human SQM2 comprises a domain near the C-terminus that contains a large number of positively-charged residues (i.e., from about residue 82 to residue 119 of SEQ ID NO:1), a feature shared in common with the human SQM1 and the B18 subunit proteins.

The amino-terminus of the human SQM2 of the present invention contains a potential myristoylation site. Myristoylation occurs on N-terminal glycine residues after removal of the initiator methionine. Residues in the second and fifth position (relative to glycine at position 1) are conserved and small and uncharged residues are preferred [Towler et al. (1988) J. Biol. Chem. 263:1784]. In the SQM2 protein the initiator methionine is followed by a glycine, and alanine and valine residues are found at positions 2 and 5; thus SQM2 follows the "rules" for myristoylation.

The human SQM2 of the present invention contains four cysteine residues ($C_{60}$, $C_{70}$, $C_{81}$, and $C_{91}$). Two of these four cysteine residues (i.e., $C_{60}$ and $C_{70}$) are conserved between the human SQM2 and SQM1 proteins (see alignment shown in FIG. 2; residues are numbered according to SEQ ID NO:1); all four of these residues are conserved between the human SQM2 and the bovine B18 subunit proteins. The human SQM2 of the present invention contains four potential O-linked glycosylation sites (i.e., serine and threonine residues). In addition, the human SQM2 of the present invention contains potential phosphorylation sites (i.e., typically the hydroxyl groups of serine, threonine and tyrosine residues although asparagine, histidine and lysine residues may also be phosphorylated).

Figure 5A:
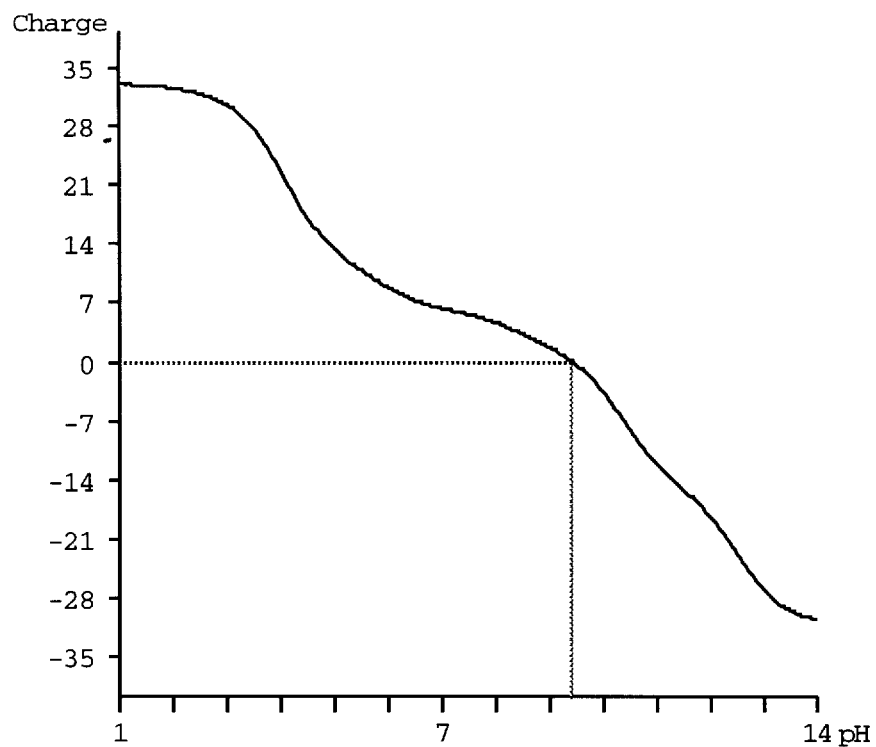
FIGS. 5A and 5B show the isoelectric plot for human SQM2 (SEQ ID NO:1) and SQM1 (SEQ ID NO:3), respectively. These plots were generated using MACDNASIS software.
Figure 5B:
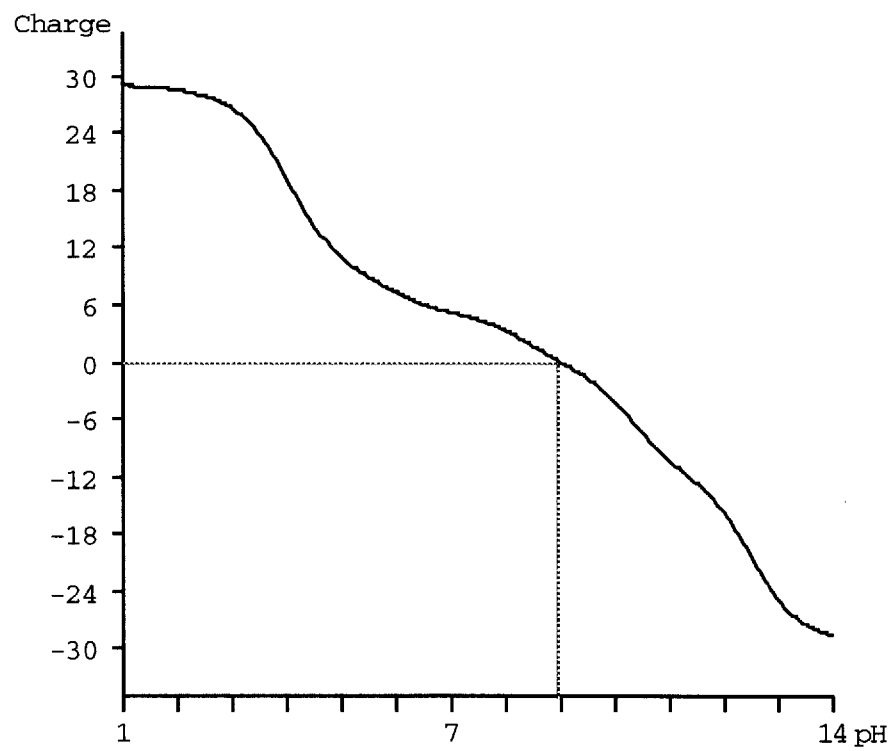

The SQM2 protein of the present invention, like the SQM1 protein has a basic isoelectric point (see FIGS. 5A and 5B). The SQM2 protein of the present invention and the human SQM1 protein have similar hydrophobicity plots (see FIGS. 4A and 4B).

The Human SQM2 Coding Sequences

The nucleic acid and deduced amino acid sequences of human SQM2 are shown in FIG. 1. In accordance with the invention, any nucleic acid sequence which encodes human SQM2 can be used to generate recombinant molecules which express human SQM2.

It will be appreciated by those skilled in the art that as a result of the degeneracy of the genetic code, a multitude of human SQM2-encoding nucleotide sequences, some bearing minimal homology to the nucleotide sequences of any known and naturally occurring gene may be produced. The invention contemplates each and every possible variation of nucleotide sequence that could be made by selecting combinations based on possible codon choices. These combinations are made in accordance with the standard triplet genetic code as applied to the nucleotide sequence encoding naturally occurring human SQM2, and all such variations are to be considered as being specifically disclosed.

Although nucleotide sequences which encode human SQM2 and its variants are preferably capable of hybridizing to the nucleotide sequence of the naturally occurring sequence under appropriately selected conditions of stringency, it may be advantageous to produce nucleotide sequences encoding human SQM2 or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding human SQM2 and its derivatives without altering the encoded amino acid sequences include the production of RNA transcripts having more desirable properties, such as a greater or a shorter half-life, than transcripts produced from the naturally occurring sequence.

It is now possible to produce a DNA sequence, or portions thereof, encoding human SQM2 and its derivatives entirely by synthetic chemistry, after which the synthetic gene may be inserted into any of the many available DNA vectors and cell systems using reagents that are well known in the art at the time of the filing of this application. Moreover, synthetic chemistry may be used to introduce mutations into a sequence encoding human SQM2 or any portion thereof.

Also included within the scope of the present invention are polynucleotide sequences that are capable of hybridizing to the nucleotide sequence of SEQ ID NO:2 under various conditions of stringency. Hybridization conditions are based on the melting temperature ($T_m$) of the nucleic acid binding complex or probe, as taught in Berger and Kimmel (1987, *Guide to Molecular Cloning Techniques, Methods in Enzymology*, Vol 152, Academic Press, San Diego, Calif.) incorporated herein by reference, and may be used at a defined "stringency".

Altered nucleic acid sequences encoding human SQM2 which may be used in accordance with the invention include deletions, insertions or substitutions of different nucleotides resulting in a polynucleotide that encodes the same or a functionally equivalent human SQM2. The protein may also show deletions, insertions or substitutions of amino acid residues which produce a silent change and result in a functionally equivalent human SQM2. Deliberate amino acid substitutions may be made on the basis of similarity in polarity, charge, solubility, hydrophobicity, hydrophilicity, and/or the amphipathic nature of the residues as long as the biological activity of human SQM2 is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine, phenylalanine, and tyrosine.

Included within the scope of the present invention are alleles encoding human SQM2. As used herein, an "allele" or "allelic sequence" is an alternative form of the nucleic acid sequence encoding human SQM2. Alleles result from a mutation, i.e., a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

Methods for DNA sequencing are well known in the art and employ such enzymes as the Klenow fragment of DNA polymerase I, SEQUENASE® (US Biochemical Corp, Cleveland Ohio), Taq DNA polymerase (Perkin Elmer, Norwalk, Conn.), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton MICROLAB 2200 (Hamilton, Reno, Nev.), Peltier Thermal Cycler (PTC200; MJ Research, Watertown, Mass.) and the ABI 377 DNA sequencers (Perkin Elmer).

Extending the Polynucleotide Sequence

The polynucleotide sequence encoding human SQM2 may be extended utilizing partial nucleotide sequence and various methods known in the art to detect upstream sequences such as promoters and regulatory elements. Gobinda et al. (1993; PCR Methods Applic 2:318–22) describe "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T. et al (1988) Nucleic Acids Res 16:8186). The primers may be designed using OLIGO® 4.06 Primer Analysis Software (1992; National Biosciences Inc, Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M. et al. (1991) PCR Methods Applic 1:111–19), a method for PCR amplification of DNA fragments adjacent to a known sequence in human and yeast artificial chromosome DNA, may also be used. Capture PCR also requires multiple restriction enzyme digestions and ligations to place an engineered double-stranded sequence into an unknown portion of the DNA molecule before PCR.

Another method which may be used to retrieve unknown sequence is walking PCR (Parker J. D. et al (1991) Nucleic Acids Res 19:3055–60), a method for targeted gene walking. Alternatively, PCR, nested primers, PROMOTER-FINDER™ (Clontech, Palo Alto, Calif.) and Promoter-Finder libraries can be used to walk in genomic DNA. This process avoids the need to screen libraries and is useful in finding intron/exon junctions.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

Capillary electrophoresis may be used to analyze either the size or confirm the nucleotide sequence in sequencing or PCR products. Systems for rapid sequencing are available from Perkin Elmer, Beckman Instruments (Fullerton, Calif.), and other companies. Capillary sequencing may employ flowable polymers for electrophoretic separation, four different fluorescent dyes (one for each nucleotide) which are laser activated, and detection of the emitted wavelengths by a charge coupled device camera. Output/light intensity is converted to electrical signal using appropriate software (e.g., GENOTYPER™ and SEQUENCE NAVIGATOR™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported [Ruiz-Martinez M. C. et al. (1993) Anal Chem 65:2851–8].

Expression of the Nucleotide Sequence

In accordance with the present invention, polynucleotide sequences which encode human SQM2, fragments of the polypeptide, fusion proteins or functional equivalents thereof may be used in recombinant DNA molecules that direct the expression of human SQM2 in appropriate host cells. Due to the inherent degeneracy of the genetic code, other DNA sequences which encode substantially the same or a functionally equivalent amino acid sequence, may be used to clone and express human SQM2. As will be understood by those of skill in the art, it may be advantageous to produce human SQM2-encoding nucleotide sequences possessing non-naturally occurring codons. Codons preferred by a particular prokaryotic or eukaryotic host [Murray E. et al. (1989) Nuc Acids Res 17:477–508] can be selected, for example, to increase the rate of human SQM2 expression or to produce recombinant RNA transcripts having desirable properties, such as a longer or a shorter half-life, than transcripts produced from naturally occurring sequence.

The nucleotide sequences of the present invention can be engineered in order to alter a human SQM2-encoding sequence for a variety of reasons, including but not limited to, alterations which modify the cloning, processing and/or expression of the gene product. For example, mutations may be introduced using techniques which are well known in the art, e.g., site-directed mutagenesis to insert new restriction sites, to alter glycosylation patterns, to change codon preference, to produce splice variants, etc.

In another embodiment of the invention, a natural, modified or recombinant human SQM2-encoding sequence may be ligated to a heterologous sequence to encode a fusion protein. For example, for screening of peptide libraries for inhibitors of human SQM2 activity, it may be useful to encode a chimeric human SQM2 protein that is recognized by a commercially available antibody. A fusion protein may also be engineered to contain a cleavage site located between a human SQM2 and the heterologous protein sequence, so that the human SQM2 may be cleaved and substantially purified away from the heterologous moiety.

In an alternate embodiment of the invention, the sequence encoding human SQM2 may be synthesized, whole or in part, using chemical methods well known in the art [see Caruthers M. H. et al. (1980) Nuc Acids Res Symp Ser 215–23, Horn T. et al. (1980) Nuc Acids Res Symp Ser 225–32, etc.]. Alternatively, the protein itself could be produced using chemical methods to synthesize a human SQM2 amino acid sequence, whole or in part. For example, peptide synthesis can be performed using various solid-phase techniques [Roberge J. Y. et al. (1995) Science 269:202–204] and automated synthesis may be achieved, for example, using the ABI 431A Peptide Synthesizer (Perkin Elmer) in accordance with the instructions provided by the manufacturer.

The newly synthesized peptide can be substantially purified by preparative high performance liquid chromatography [e.g., Creighton (1983) Proteins, Structures and Molecular Principles, W. H. Freeman and Co., New York, N.Y.]. The composition of the synthetic peptides may be confirmed by amino acid analysis or sequencing (e.g., the Edman degradation procedure; Creighton, supra). Additionally the amino acid sequence of human SQM2, or any part thereof, may be altered during direct synthesis and/or combined using chemical methods with sequences from other proteins, or any part thereof, to produce a variant polypeptide.

Expression Systems

In order to express a biologically active human SQM2, the nucleotide sequence encoding human SQM2 or its functional equivalent, is inserted into an appropriate expression vector, i.e., a vector which contains the necessary elements for the transcription and translation of the inserted coding sequence.

Methods which are well known to those skilled in the art can be used to construct expression vectors containing a human SQM2-encoding sequence and appropriate transcriptional or translational controls. These methods include in vitro recombinant DNA techniques, synthetic techniques and in vivo recombination or genetic recombination. Such techniques are described in Sambrook et al. (1989) *Molecular Cloning, A Laboratory Manual,* Cold Spring Harbor Press, Plainview, N.Y. and Ausubel F. M. et al. (1989) *Current Protocols in Molecular Biology,* John Wiley & Sons, New York, N.Y.

A variety of expression vector/host systems may be utilized to contain and express a human SQM2-encoding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems.

The "control elements" or "regulatory sequences" of these systems vary in their strength and specificities and are those nontranslated regions of the vector, enhancers, promoters, and 3' and 5' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT® phagemid (Stratagene, LaJolla, Calif.) or PSPORT1 (Gibco BRL) and ptrp-lac hybrids and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from the mammalian genes or from mammalian viruses are most appropriate. If it is necessary to generate a cell line that contains multiple copies of the sequence encoding human SQM2, vectors based on SV40 or EBV may be used with an appropriate selectable marker.

In bacterial systems, a number of expression vectors may be selected depending upon the use intended for human SQM2. For example, when large quantities of human SQM2 are needed for the induction of antibodies, vectors which direct high level expression of fusion proteins that are readily purified may be desirable. Such vectors include, but are not limited to, the multifunctional *E. coli* cloning and expression vectors such as BLUESCRIPT® (Stratagene), in which the sequence encoding human SQM2 may be ligated into the vector in frame with sequences for the amino-terminal Met and the subsequent 7 residues of β-galactosidase so that a hybrid protein is produced; pIN vectors [Van Heeke & Schuster (1989) J Biol Chem 264:5503–5509]; and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor Xa protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase and PGH may be used. For reviews, see Ausubel et al. (supra) and Grant et al. (1987) Methods in Enzymology 153:516–544.

In cases where plant expression vectors are used, the expression of a sequence encoding human SQM2 may be driven by any of a number of promoters. For s example, viral promoters such as the 35S and 19S promoters of CaMV [Brisson et al. (1984) Nature 310:511–514] may be used alone or in combination with the omega leader sequence from TMV [Takamatsu et al. (1987) EMBO J 6:307–311]. Alternatively, plant promoters such as the small subunit of RUBISCO [Coruzzi et al (1984) EMBO J 3:1671–1680; Broglie et al. (1984) Science 224:838–843]; or heat shock promoters [Winter J. and Sinibaldi R. M. (1991) Results Probl Cell Differ 17:85–105] may be used. These constructs can be introduced into plant cells by direct DNA transformation or pathogen-mediated transfection. For reviews of such techniques, see Hobbs S. or Murry L. E. in *McGraw Hill Yearbook of Science and Technology* (1992) McGraw Hill New York, N.Y., pp 191–196 or Weissbach and Weissbach (1988) *Methods for Plant Molecular Biology,* Academic Press, New York, N.Y., pp 421–463.

An alternative expression system which could be used to express human SQM2 is an insect system. In one such system, *Autographa californica* nuclear polyhedrosis virus (AcNPV) is used as a vector to express foreign genes in *Spodoptera frugiperda* cells or in Trichoplusia larvae. The sequence encoding human SQM2 may be cloned into a nonessential region of the virus, such as the polyhedrin gene, and placed under control of the polyhedrin promoter. Successful insertion of the sequence encoding human SQM2 will render the polyhedrin gene inactive and produce recombinant virus lacking coat protein. The recombinant viruses are then used to infect *S. frugiperda* cells or Trichoplusia larvae in which human SQM2 is expressed [Smith et al. (1983) J Virol 46:584; Engelhard E. K. et al. (1994) Proc Natl Acad Sci 91:3224–7].

In mammalian host cells, a number of viral-based expression systems may be utilized. In cases where an adenovirus is used as an expression vector, a sequence encoding human SQM2 may be ligated into an adenovirus transcription/translation complex consisting of the late promoter and tripartite leader sequence. Insertion in a nonessential E1 or E3 region of the viral genome will result in a viable virus capable of expressing in infected host cells [Logan and Shenk (1984) Proc Natl Acad Sci 81:3655–59]. In addition, transcription enhancers, such as the Rous sarcoma virus (RSV) enhancer, may be used to increase expression in mammalian host cells.

Specific initiation signals may also be required for efficient translation of a sequence encoding human SQM2. These signals include the ATG initiation codon and adjacent sequences. In cases where the sequence encoding human SQM2, its initiation codon and upstream sequences are inserted into the most appropriate expression vector, no additional translational control signals may be needed. However, in cases where only coding sequence, or a portion thereof, is inserted, exogenous translational control signals including the ATG initiation codon, and termination codons must be provided. Furthermore, the initiation codon must be in the correct reading frame to ensure translation of the entire insert. Exogenous translational elements and initiation codons can be of various origins, both natural and synthetic. The efficiency of expression may be enhanced by the inclusion of enhancers appropriate to the cell system in use [Scharf D. et al. (1994) Results Probl Cell Differ 20:125–62; Bittner et al. (1987) Methods in Enzymol 153:516–544].

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO (ATCC CCL 61 and CRL 9618), HeLa (ATCC CCL 2), MDCK (ATCC CCL 34 and CRL 6253), HEK 293 (ATCC CRL 1573), WI-38 (ATCC CCL 75) (ATCC: American Type Culture Collection, Rockville, Md.), etc. have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express human SQM2 may be transformed using expression vectors which contain endogenous expression elements, and may also contain viral origins of replication and a selectable marker gene; the selectable marker gene may be located on the same vector as the SQM2-encoding sequences or may be located on a separate vector which contains sequences which permit expression of the selectable marker gene. Following the introduction of the vector(s), cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transfected cells can be proliferated using tissue culture techniques appropriate to the cell type.

Any number of selection systems may be used to recover transfected cell lines. These include, but are not limited to, the herpes simplex virus thymidine kinase (Wigler M. et al. (1977) Cell 11:223–32) and adenine phosphoribosyltransferase (Lowy I. et al. (1980) Cell 22:817–23) genes which can be employed in tk- or aprt-cells, respectively. Also, antimetabolite, antibiotic or herbicide resistance can be used as the basis for selection; for example, dhfr which confers resistance to methotrexate [Wigler M. et al. (1980) Proc Natl Acad Sci 77:3567–70]; npt, which confers resistance to the aminoglycosides neomycin and G-418 [Colbere-Garapin F. et al. (1981) J Mol Biol 150:1–14] and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine [Hartman S. C. and R. C. Mulligan (1988) Proc Natl Acad Sci 85:8047–51]. Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system [Rhodes C. A. et al. (1995) Methods Mol Biol 55:121–131].

Identification of Transfectants Containing the Polynucleotide Sequence

Although the presence/absence of marker gene expression suggests that the gene of interest is also present, its presence and expression should be confirmed. For example, if the sequence encoding human SQM2 is inserted within a marker gene sequence, recombinant cells containing the sequence encoding human SQM2 can be identified by the absence of marker gene function. Alternatively, a marker gene can be placed in tandem with the sequence encoding human SQM2 under the control of a single promoter. Expression of the marker gene in response to induction or selection usually indicates expression of the tandem sequence as well.

Alternatively, host cells which contain the coding sequence for human SQM2 and express human SQM2 may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the polynucleotide sequence encoding human SQM2 can be detected by DNA-DNA or DNA-RNA hybridization or amplification using probes, portions or fragments of the sequence encoding human SQM2. Nucleic acid amplification based assays involve the use of oligonucleotides or oligomers based on the nucleic acid sequence to detect transformants containing DNA or RNA encoding human SQM2. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of human SQM2, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on human SQM2 is preferred, but a competitive binding assay may be employed. These and other assays are described, among other places, in Hampton R. et al. (1990, *Serological Methods a Laboratory Manual,* APS Press, St. Paul, Minn.) and Maddox D. E. et al. (1983, J Exp Med 158:1211).

A wide variety of labels and conjugation techniques are known by those skilled in the art and can be used in various nucleic acid and amino acid assays. Means for producing labeled hybridization or PCR probes for detecting related sequences include oligolabeling, nick translation, end-labeling or PCR amplification using a labeled nucleotide. Alternatively, the human SQM2-encoding sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway, N.J.), Promega (Madison, Wis.), and US Biochemical Corp (Cleveland, Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like.

Purification of Human SQM2

Host cells transformed with a nucleotide sequence encoding human SQM2 may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing human SQM2-encoding sequence can be designed with signal sequences which direct secretion of human SQM2 through a prokaryotic or eukaryotic cell membrane. Further, the art understands that where secretion of human SQM2 is not desired, sequences encoding a signal sequence are not employed on expression vectors containing human SQM2 gene sequences.

Human SQM2 may also be expressed as a recombinant protein with one or more additional polypeptide domains added to facilitate purification of soluble proteins. Such purification facilitating domains include, but are not limited to, metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle, Wash.). The inclusion of a cleavable linker sequences such as Factor Xa or enterokinase (Invitrogen, San Diego, Calif.) between the purification domain and human SQM2 is useful to facilitate purification. One such expression vector provides for expression of a fusion protein comprising the sequence encoding human SQM2 and nucleic acid sequence encoding 6 histidine residues followed by thioredoxin and an enterokinase cleavage site. The histidine residues facilitate purification while the enterokinase cleavage site provides a means for purifying human SQM2 from the fusion protein. Literature pertaining to vectors containing fusion proteins is available in the art [see, for example, Kroll D. J. et al. (1993) DNA Cell Biol 12:441–53].

In addition to recombinant production, fragments of human SQM2 may be produced by direct peptide synthesis using solid-phase techniques [cf Stewart et al. (1969) *Solid-Phase Peptide Synthesis,* W. H. Freeman Co., San Francisco; Merrifield J. (1963) J Am Chem Soc 85:2149–2154]. In vitro protein synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer. Various fragments of human SQM2 may be chemically synthesized separately and combined using chemical methods to produce the full length molecule.

Uses of Human SQM2

The rationale for use of the nucleotide and peptide sequences disclosed herein is based in part on the chemical and structural homology among the novel human SQM2 protein of the present invention and the human SQM1 protein [GI 180233; Wong et al. (1990), supra]. In addition, the novel human SQM2 protein, like the SQM1 protein, shares chemical and structural homology with the B18 subunit of the bovine NADH:ubiquinone oxidoreductase [GI 244; Walker et al. (1992), supra].

Human SQM1 is a cell adhesion molecule located on the surface of squamous epithelial cells, including squamous carcinoma cells. Cell adhesion molecules are involved in a wide variety of important cellular functions including cell-cell and cell-matrix interactions; aberrant expression of some cell adhesion molecules is associated with disease including tumorigenesis and/or metastasis. For example, the human genetic diseases, Glanzmann's thrombasthenia and leukocyte adhesion deficiency, affect members of the integrin family, a class of cell adhesion molecules [Hynes (1987), supra]. The human SQM1 protein has been shown to be involved in cell adhesion of squamous epithelial cells, endothelial cells and extracellular matrix proteins. Antibodies directed against SQM1 preferentially inhibit adhesion interactions between epithelial and endothelial cells and between epithelial cells and extracellular matrix proteins (e.g., fibronectin and collagen) [Wong et al. (1990), supra]. This data supports a role for SQM1 in the metastasis of epithelial tumors.

Epithelial cells form membranes which line or cover numerous tissues; all materials that enter or exit the body do so through an epithelial membrane. Epithelial cells also form endocrine and exocrine glands. Epithelial cells are classified into squamous, cuboidal, columnar and transitional. The following provides a non-exhaustive list of locations where squamous epithelial cells are found: the pulmonary alveoli, the endothelial lining of blood vessels, the mesothelium which covers or lines the body cavities, the Bowman's capsule and loop of Henle in the kidney, the esophagus, cornea, vagina and the epidermis [Text/Atlas of Histology, Leeson et al., W. B. Saunders Co., Philadelphia, Pa. (1988), p. 125].

As demonstrated herein, the human SQM2 of the present invention is expressed in colon, wrist synovium, breast, brain, and lung. The colon library was constructed using tissue from a patient suffering from Crohn's disease, an inflammatory bowel disease. Squamous cell carcinoma (SCC) of the colon occurs in patients with inflammatory bowel disease; SCC also occurs as a primary tumor which rapidly metastasizes [Vraux et al. (1994) Acta Chir. Belg. 94:318]. While the tissue used for the colon library was taken from an area which by visual appearance was uninvolved in disease, it is possible that this tissue contained some cells affected by Crohn's disease.

The lung is also known to develop squamous cell carcinoma [Rosado-de-Christenson et al. (1994) Radiographics 14:429 and Keita et al. (1995) Med. Pediatr. Oncol. 24:50]. In addition, the pulmonary alveoli of the normal lung comprises squamous epithelial cells.

Cell adhesion molecules have been implicated in facilitating the adherence of malignant cells to the extracellular matrix during tumor metastases. These cell adhesion molecules include SQM1 [Wong et al. (1990), supra] and CDw44, a lymphocyte adhesion protein whose expression is elevated in colon carcinomas [Stamenkovic et al. (1989) cell 56:1057]. Other cell adhesion molecules affected by disease include the integrins which are involved in Glanzmann's thrombasthenia and leukocyte adhesion deficiency [Hynes (1987), supra]. Thus, the novel human SQM2 nucleic and amino acid sequences of the present invention are useful in the development of diagnostics for the detection of tumors and other diseases. The nucleotide sequence may be used in hybridization or PCR technologies to diagnose the induced expression of SQM2 sequences early in the disease process. Likewise the protein can be used to produce antibodies useful in ELISA assays or a derivative diagnostic format (as discussed in detail below).

In one embodiment of the diagnostic method of the present invention, normal or standard values for human SQM2 mRNA expression are established as a baseline. This can be accomplished by a number of assays such as quantitating the amount of SQM2 mRNA in tissues taken from normal subjects, either animal or human, with nucleic probes derived from the SQM2 sequences provided herein (either DNA or RNA forms) using techniques which are well known in the art (e.g., Southern blots, Northern blots, dot or slot blots). The standard values obtained from normal samples may be compared with values obtained from samples from subjects potentially affected by disease (e.g., tumors). Deviation between standard and subject values can establish the presence of a disease state. In addition, the deviation can indicate, within a disease state, a particular clinical outcome (e.g., metastatic or non-metastatic).

The nucleotide sequence encoding human SQM2 is useful when placed in an expression vector for making quantities of protein for therapeutic use. The antisense nucleotide sequence of the human SQM2 gene is potentially useful in vectors designed for gene therapy directed at neoplasia including metastases. Additionally, the inhibition of human SQM2 expression may be useful in detecting the development of disturbances in MTX transport which leads to MTX resistance during chemotherapy. Alternatively, the human SQM2-encoding nucleotide sequence may be used to direct the expression of human SQM2 in situations where it is desirable to increase the amount of human SQM2 (e.g., for disorders associated with low or nonexistent level of expression of SQM2 such as the development of MTX resistance). Even the transient expression or delivery of human SQM2 to cells and tissues may be therapeutic.

Human SQM2 Antibodies

Human SQM2-specific antibodies are useful for the diagnosis and treatment of conditions and diseases associated with expression of human SQM2 (including the overexpression and the absence of expression). Such antibodies include, but are not limited to, polyclonal, monoclonal, chimeric, single chain, Fab fragments and fragments produced by a Fab expression library. Neutralizing antibodies, i.e., those which inhibit dimer formation, are especially preferred for diagnostics and therapeutics.

Human SQM2 protein to be used for antibody induction need not retain biological activity; however, the protein fragment, or oligopeptide must be antigenic. Peptides used to induce specific antibodies may have an amino acid sequence consisting of at least five amino acids, preferably at least 10 amino acids. Preferably, they should mimic a portion of the amino acid sequence of the natural protein and may contain the entire amino acid sequence of a small, naturally occurring molecule. Short stretches of human SQM2 amino acids may be fused with those of another protein such as keyhole limpet hemocyanin and antibody produced against the chimeric molecule.

For the production of antibodies, various hosts including goats, rabbits, rats, mice, etc. may be immunized by injection with human SQM2 or any portion, fragment or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (Bacillus Calmette-Guerin) and *Corynebacterium parvum* are potentially useful adjuvants.

Monoclonal antibodies to human SQM2 may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique [Cole et al. (1985) *Monoclonal Antibodies and Cancer Therapy*, Alan R Liss Inc., New York, N.Y., pp 77–96].

In addition, techniques developed for the production of "chimeric antibodies", the splicing of mouse antibody genes to human antibody genes to obtain a molecule with appropriate antigen specificity and biological activity can be used [Morrison et al. (1984) Proc Natl Acad Sci 81:6851–6855; Neuberger et al. (1984) Nature 312:604–608; Takeda et al. (1985) Nature 314:452–454]. Alternatively, techniques described for the production of single chain antibodies (U.S. Pat. No. 4,946,778) can be adapted to produce human SQM2-specific single chain antibodies.

Antibodies may also be produced by inducing in vivo production in the lymphocyte population or by screening recombinant immunoglobulin libraries or panels of highly specific binding reagents as disclosed in Orlandi et al. (1989, Proc Natl Acad Sci 86:3833–3837), and Winter G. and Milstein C. (1991; Nature 349:293–299).

Antibody fragments which contain specific binding sites for human SQM2 may also be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity [Huse W. D. et al. (1989) Science 256:1275–1281].

A variety of protocols for competitive binding or immunoradiometric assays using either polyclonal or monoclonal antibodies with established specificities are well known in the art. Such immunoassays typically involve the formation of complexes between human SQM2 and its specific antibody and the measurement of complex formation. A two-site, monoclonal-based immunoassay utilizing monoclonal antibodies reactive to two noninterfering epitopes on a specific human SQM2 protein is preferred, but a competitive binding assay may also be employed. These assays are described in Maddox D. E. et al. (1983, J Exp Med 158:1211).

Diagnostic Assays Using Human SQM2 Specific Antibodies

Particular human SQM2 antibodies are useful for the diagnosis of conditions or diseases characterized by expression of human SQM2 or in assays to monitor patients being treated with human SQM2, its fragments, agonists or inhibitors (including antisense transcripts capable of reducing expression of human SQM2). Diagnostic assays for human SQM2 include methods utilizing the antibody and a label to detect human SQM2 in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring human SQM2, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on human SQM2 is preferred, but a competitive binding assay may be employed. These assays are described, among other places, in Maddox, D. E. et al. (1983, J Exp Med 158:1211).

In order to provide a basis for diagnosis, normal or standard values for human SQM2 expression must be established. This is accomplished by combining body fluids or cell extracts taken from normal subjects, either animal or human, with antibody to human SQM2 under conditions suitable for complex formation which are well known in the art. The amount of standard complex formation may be quantified by comparing various artificial membranes containing known quantities of human SQM2 with both control and disease samples from biopsied tissues. Then, standard values obtained from normal samples may be compared with values obtained from samples from subjects potentially affected by disease (e.g., metastases). Deviation between standard and subject values establishes the presence of a disease state.

Drug Screening

Human SQM2, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between human SQM2 and the agent being tested, may be measured.

Another technique for drug screening which may be used for high throughput screening of compounds having suitable binding affinity to the human SQM2 is described in detail in "Determination of Amino Acid Sequence Antigenicity" by Geysen H. N., WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of human SQM2 and washed. Bound human SQM2 is then detected by methods well known in the art. Substantially purified human SQM2 can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding human SQM2 specifically compete with a test compound for binding human SQM2. In this manner, the antibodies can be used to detect the presence of any peptide which shares one or more antigenic determinants with human SQM2.

Uses of the Polynucleotide Encoding Human SQM2

A polynucleotide sequence encoding human SQM2 or any part thereof may be used for diagnostic and/or therapeutic purposes. For diagnostic purposes, the sequence encoding human SQM2 of this invention may be used to detect and quantitate gene expression in biopsied tissues in which human SQM2 may be expressed. The diagnostic assay is useful to distinguish between absence, presence, and excess expression (i.e., overexpression) of human SQM2 and to monitor regulation of human SQM2 levels during therapeutic intervention. Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding human SQM2 or closely related molecules. The specificity of the probe, whether it is made from a highly specific region, e.g., 10 unique nucleotides in the 5' regulatory region, or a less specific region, e.g., especially in the 3' region, and the stringency of the hybridization or amplification (maximal, high, intermediate or low) will determine whether the probe identifies only naturally occurring human SQM2, alleles or related sequences.

Probes may also be used for the detection of related sequences and should preferably contain at least 50% of the nucleotides from any of these human SQM2-encoding sequences. The hybridization probes of the subject invention may be derived from the nucleotide sequence of SEQ ID NO:2 or from genomic sequence including promoter, enhancer elements and introns of the naturally occurring sequence encoding human SQM2. Hybridization probes may be labeled by a variety of reporter groups, including radionuclides such as $^{32}$p or $^{35}$S, or enzymatic labels such as alkaline phosphatase coupled to the probe via avidin/biotin coupling systems, and the like.

Other means for producing specific hybridization probes for DNAs include the cloning of nucleic acid sequences encoding human SQM2 or human SQM2 derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

Diagnostic Use

Polynucleotide sequences encoding human SQM2 may be used for the diagnosis of conditions or diseases with which the expression of human SQM2 is associated. For example, polynucleotide sequences encoding human SQM2 may be used in hybridization or PCR assays of fluids or tissues from biopsies to detect human SQM2 expression. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits.

The human SQM2-encoding nucleotide sequences disclosed herein provide the basis for assays that detect activation or induction associated with disease (including metastasis); in addition, the lack of expression of human SQM2 may be detected using the human SQM2-encoding nucleotide sequences disclosed herein. The nucleotide sequence may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of nucleotide sequences encoding human SQM2 in the sample indicates the presence of the associated disease. Alternatively, the loss of expression of human SQM2 sequences in a tissue which normally expresses human SQM2 sequences indicates the presence of an abnormal or disease state.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for human SQM2 expression must be established. This is accomplished by combining body fluids or cell extracts taken from normal subjects, either animal or human, with human SQM2, or a portion thereof, under conditions suitable for hybridization or amplification. Standard hybridization may be quantified by comparing the values obtained for normal subjects with a dilution series of human SQM2 run in the same experiment where a known amount of substantially purified human SQM2 is used. Standard values obtained from normal samples may be compared with values obtained from samples from patients affected by human SQM2-associated diseases. Deviation between standard and subject values establishes the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR, may be used and provides additional uses for oligonucleotides based upon the sequence encoding human SQM2. Such oligomers are generally chemically synthesized, but they may be generated enzymatically or produced from a recombinant source. Oligomers generally comprise two nucleotide sequences, one with sense orientation (5'-3') and one with antisense (3'-5'), employed under optimized conditions for identification of a specific gene or condition. The same two oligomers, nested sets of oligomers, or even a degenerate pool of oligomers may be employed under less stringent conditions for detection and/ or quantitation of closely related DNA or RNA sequences.

Additionally, methods which may be used to quantitate the expression of a particular molecule include radiolabeling [Melby P. C. et al (1993) J Immunol Methods 159:235–44] or biotinylating [Duplaa C. et al. (1993) Anal Biochem 229–36] nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Therapeutic Use

Based upon its homology to human SQM1 and its expression profile, the polynucleotide encoding human SQM2 disclosed herein may be useful in the treatment of metastasis particularly of epithelial tumors; in particular, inhibition of human SQM2 expression may be therapeutic. In addition, as the reduced expression of SQM1 has been shown to correlate with the development of MTX resistance in squamous carcinoma cells, increased expression of SQM2 in tissues exposed to MTX (i.e., restoration of SQM2 to normal or pretreatment levels) may be therapeutic.

Expression vectors derived from retroviruses, adenovirus, herpes or vaccinia viruses, or from various bacterial plasmids, may be used for delivery of nucleotide sequences (sense or antisense) to the targeted organ, tissue or cell population. Methods which are well known to those skilled in the art can be used to construct recombinant vectors which will express antisense of the sequence encoding human SQM2. See, for example, the techniques described in Sambrook et al. (supra) and Ausubel et al. (supra).

The polynucleotides comprising full length cDNA sequence and/or its regulatory elements enable researchers to use the sequence encoding human SQM2 as an investigative tool in sense [Youssoufian H. and H. F. Lodish 1993 Mol Cell Biol 13:98–104] or antisense [Eguchi et al. (1991) Annu Rev Biochem 60:631–652] regulation of gene function. Such technology is now well known in the art, and sense or antisense oligomers, or larger fragments, can be designed from various locations along the coding or control regions.

Genes encoding human SQM2 can be turned off by transfecting a cell or tissue with expression vectors which express high levels of a desired human SQM2 fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA or PNA, to the control regions of the sequence encoding human SQM2, i.e., the promoters, enhancers, and introns. Oligonucleotides derived from the transcription initiation site, e.g., between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J. E. et al. [In: Huber B. E. and B. I. Carr (1994) *Molecular and Immunologic Approaches*, Futura Publishing Co., Mt. Kisco, N.Y.].

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of the sequence encoding human SQM2.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding human SQM2. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient is presented in U.S. Pat. Nos. 5,399,493 and 5,437,994, disclosed herein by reference. Delivery by transfection and by liposome are quite well known in the art.

Furthermore, the nucleotide sequences encoding human SQM2 disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence encoding human SQM2 can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price C. M. (1993; Blood Rev 7:127–34) and Trask B. J. (1991; Trends Genet 7:149–54).

The technique of fluorescent in situ hybridization (FISH) of chromosome spreads has been described, among other places, in Verma et al. (1988) *Human Chromosomes: A Manual of Basic Techniques,* Pergamon Press, New York, N.Y. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a the sequence encoding human SQM2 on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers are invaluable in extending genetic maps. A recent example of an STS based map of the human genome was recently published by the Whitehead-MIT Center for Genomic Research [Hudson T. J. et al. (1995) Science 270:1945–1954]. Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 [Gatti et al. (1988) Nature 336:577–580], any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention relates to pharmaceutical compositions which may comprise nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that known in the art, e.g., by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of human SQM2, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, e.g., tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for nucleotides than for proteins or their inhibitors. Similarly, delivery of polynucleotides or polypeptides will be specific to particular cells, conditions, locations, etc.

It is contemplated, for example, that human SQM2 can be used as a therapeutic molecule to maintain or restore the ability of cells to transport MTX. It is further contemplated that antisense molecules capable of reducing the expression of human SQM2 can be as therapeutic molecules to treat tumors associated with the aberrant expression of human SQM2. Still further it is contemplated that antibodies directed against human SQM2 and capable of neutralizing the biological activity of human SQM2 may be used as therapeutic molecules to treat tumors associated with the aberrant expression of human SQM2.

The examples below are provided to illustrate the subject invention and are not included for the purpose of limiting the invention.

EXAMPLES

I. SYNORAT03 cDNA Library Construction

The rheumatoid wrist synovium from a 56 year-old female was used for cDNA library construction and was obtained from T. Kenny, Univ. of Calif. Davis (Davis, Calif.). The frozen tissue was homogenized using a Brinkmann Homogenizer Polytron PT-3000 (Brinkmann Instruments, Westbury, N.J.) and lysed in a buffer containing guanidinium isothiocyanate. The lysate was centrifuged over a 5.7M CsCl cushion using a Beckman SW28 rotor in a Beckman L8-70M Ultracentrifuge (Beckman Instruments) for 18 hours at 25,000 rpm at ambient temperature. The RNA was extracted twice with acid phenol pH 4.0 using the reagents and extraction procedures as supplied in the STRATAGENE RNA Isolation Kit (Catalog # 200345; Stratagene). RNA was precipitated using 0.3M sodium acetate and 2.5 volumes of ethanol, resuspended in water and DNase treated for 15 min at 37° C. The RNA was isolated using the QIAGEN OLIGOTEX kit (QIAGEN Inc., Chatsworth, Calif.) and used to construct the cDNA library.

The RNA was used to construct cDNAs according to the recommended protocols in the Plasmid System for cDNA Synthesis and Plasmid Cloning (Catalog #18248-013, Gibco BRL, Grand Island, N.Y.). cDNAs were fractionated on a Sepharose CL4B column (Catalog #275105, Pharmacia) to obtain sequences exceeding 400 bp and ligated into the plasmid, pSport I. The plasmid was subsequently transformed into DH5α™ competent cells (Catalog #18258-012, Gibco BRL) for amplification.

II. Isolation and Sequencing of cDNA Clones

Plasmid DNA was released from the cells and purified using the Miniprep Kit (Catalog #77468; Advanced Genetic Technologies Corporation, Gaithersburg, Md.). This kit consists of a 96-well block with reagents for 960 purifications. The recommended protocol was employed except for the following changes: 1) the 96 wells were each filled with only 1 ml of sterile Terrific Broth (Catalog #22711, Life Technologies, Gaithersburg, Md.) with carbenicillin at 25 mg/L and glycerol at 0.4%; 2) the bacteria were cultured for 24 hours after the wells were inoculated and then lysed with 60 µl of lysis buffer; 3) a centrifugation step employing the Beckman GS-6R rotor at 2900 rpm for 5 minutes was performed before the contents of the block were added to the primary filter plate; and 4) the optional step of adding isopropanol to TRIS buffer was not routinely performed. After the last step in the protocol, samples were transferred to a Beckman 96-well block for storage.

The cDNAs were sequenced by the method of Sanger F. and A. R. Coulson (1975; J Mol Biol 94:441f), using a Hamilton Micro Lab 2200 (Hamilton, Reno, Nev.) in combination with four Peltier Thermal Cyclers (PTC200 from MJ Research, Watertown, Mass.) and Applied Biosystems 377 or 373 DNA Sequencing Systems, and the reading frame was determined.

III. Homology Searching of cDNA Clones and Their Deduced Proteins

Each cDNA was compared to sequences in GenBank using a search algorithm developed by Applied Biosystems and incorporated into the INHERIT-670 Sequence Analysis System. In this algorithm, Pattern Specification Language (TRW Inc., Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul S. F. (1993) J Mol Evol 36:290–300; Altschul, S. F. et al. (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

A comparison of the full-length and partial cDNA sequences and the deduced amino acid sequences corresponding to the human SQM2 gene and SQM2 protein with known nucleotide and protein sequences in GenBank revealed that the full-length human SQM2 cDNA and protein sequences (i.e., SEQ ID NOS:1 and 2) were unique (i.e., not previously identified). Thus, SEQ ID NO:1 represents the first identified human SQM2 homolog. This search revealed that the human SQM2 protein shared some homology with the human SQM1 (see alignment in FIG. 2) and the B18 subunit of the bovine NADH:ubiquinone oxidoreductase.

II. Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul S. F. 1993 and 1990, supra) are used to search for identical or related molecules in nucleotide databases such as GenBank or the LIFESEQ® database (Incyte, Palo Alto, Calif.) (this technique is termed an "electronic northern"). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

and it takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

Electronic northern analysis (FIG. 3) revealed that mRNA encoding human SQM2 (SEQ ID NO:1) was present in libraries generated from the following tissues: colon (Incyte library: COLNNOT05); synovium (Incyte library: SYNORAT03); and breast (Incyte library: BRSTNOT03). This analysis revealed that human SQM2 transcripts were most abundant in the colon. In addition, partial cDNAs corresponding to the SQM2 gene were found in libraries constructed using brain (Incyte library: BRAINOT09) and lung (Incyte library: LUNGNOT10).

III. Extension of the Sequence Encoding Human SQM2

The nucleic acid sequence of SEQ ID NO:2 is used to design oligo-nucleotide primers for extending a partial nucleotide sequence to full length or for obtaining 5' sequence from genomic libraries. One primer is synthesized to initiate extension in the antisense direction (XLR) and the other is synthesized to extend sequence in the sense direction (XLF). Primers allow the extension of the know sequence "outward" generating amplicons containing new, unknown nucleotide sequence for the region of interest. The initial primers are designed from the cDNA using OLIGO® 4.06 Primer Analysis Software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; MJ Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture is analyzed by electrophoresis on a low concentration (about 0.6–0.8%) agarose mini-gel to determine which reactions were successful in extending the sequence. Bands thought to contain the largest products are selected and cut out of the gel. Further purification involves using a commercial gel extraction method such as QIAQUICK™ (QIAGEN Inc.). After recovery of the DNA, Klenow enzyme is used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent E. coli cells (in 40 µl of appropriate media) are transformed with 3 µl of ligation mixture and cultured in 80 µl of SOC medium (Sambrook J. et al., supra). After incubation for one hour at 37° C., the whole transformation mixture is plated on Luria Bertani (LB)-agar (Sambrook J. et al., supra) containing 2×Carb. The following day, several colonies are randomly picked from each plate and cultured in 150 µl of liquid LB/2×Carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer and one or both of the gene specific primers used for the extension reaction are added to each well.

Amplification is performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

IV. Labeling and Use of Hybridization Probes

Hybridization probes derived from SEQ ID NO:2 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 National Biosciences), labeled by combining 50 pmol of each oligomer and 250 mCi of $[\gamma$-$^{32}P]$ adenosine triphosphate (Amersham, Chicago, Ill.) and T4 polynucleotide kinase (DuPont NEN®, Boston, Mass.). The labeled oligonucleotides are substantially purified with Sephadex G-25 super fine resin column (Pharmacia). A portion containing $10^7$ counts per minute of each of the sense and antisense oligonucleotides is used in a typical membrane based hybridization analysis of human genomic DNA digested with one of the following endonucleases (AseI, BglII, EcoRI, PstI, XbaI, or PvuII; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

V. Antisense Molecules

The sequence encoding human SQM2, or any part thereof, is used to inhibit in vivo or in vitro expression of the naturally occurring sequence. Although use of antisense oligonucleotides, comprising about 20 base-pairs, is specifically described, essentially the same procedure is used with larger cDNA fragments. An oligonucleotide complementary to the coding sequence of human SQM2 as shown in FIG. 1 is used to inhibit expression of the naturally occurring sequence. The complementary oligonucleotide is designed from the most unique 5' sequence as shown in FIG. 1 and used either to inhibit transcription by preventing promoter binding to the upstream nontranslated sequence or translation of an human SQM2-encoding transcript by preventing the ribosome from binding. Using an appropriate portion of the leader and 5' sequence of SEQ ID NO:2, an effective antisense oligonucleotide includes any 15–20 nucleotides spanning the region which translates into the signal or early coding sequence of the polypeptide as shown in FIG. 1.

VI. Expression of Human SQM2

Expression of the human SQM2 is accomplished by subcloning the cDNAs into appropriate vectors and transfecting the vectors into host cells. In this case, the cloning vector, pSport1, previously used for the generation of the cDNA library is used to express human SQM2 in E. coli. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a polylinker containing a number of unique restriction sites.

Induction of an isolated, transfected bacterial strain with IPTG using standard methods produces a fusion protein which consists of the first seven residues of β-galactosidase, about 5 to 15 residues of linker, and the full length human SQM2. The signal sequence provided by the vector directs the secretion of human SQM2 into the bacterial growth media which can be used directly in the following assay for activity.

In addition, the human SQM2 protein may be expressed as a fusion protein containing a histidine tag or GST tag using commercially available expression vectors [e.g., QIAexpress vectors (Qiagen) and pGex vectors (Pharmacia), respectively]. Suitable host cells and conditions for the induction/expression of the desired expression vectors are known to the art and available commercially. Histidine tagged human SQM2 may be purified from *E. coli* extracts using metal chelation chromatography using commercially available resins [e.g., Ni-NTA Agarose (Qiagen)]. GST-tagged human SQM2 may be purified from *E. coli* extracts using affinity chromatography using commercially available resins [e.g., glutathione-SEPHAROSE beads (Pharmacia)]. Several other expression systems are available and may be employed to express fusion proteins comprising human SQM2 (e.g., pMAL vectors from New England Biolabs, Beverly, Mass.).

VII. Assay for Human SQM2 Activity

The ability of human SQM2 to mediate cell adhesion can be demonstrated by expression of SQM2 in cells which do not naturally express SQM2 and showing that expression of SQM2 permits these cells to adhere to endothelial cells and/or extracellular matrix proteins (e.g., collagen, fibronectin). Mammalian cell lines which do not express SQM2 (SQM2⁻ cell lines) are identified by conventional means (e.g., Northern, dot or slot blots of RNA probed with SQM2 gene sequences, lack of reactivity of the cell surface suing anti-SQM2 antibodies). An expression vector capable of directing the expression of SQM2 in the SQM2⁻ cell lines chosen is introduced into the SQM2⁻ cell lines under conditions which permit the expression of SQM2. SQM2⁻ cell lines which received the SQM2 expression vector and SQM2⁻ cell lines which did not receive the SQM2 expression vector are then used in cell adhesion studies [e.g., as described in Wong et al. (1990), supra]. For example, the cells (SQM2+ and SQM2⁻ cells) are preincubated with an anti-SQM2 antibody for one hour. Normal serum or an irrelevant antibody is used on separate aliquots of the cells as a control. After this preincubation step, the cells are washed with medium and then the cells are labeled with a fluorescent dye (e.g., Rh-123) followed by washing with medium. The labelled cells are added to coverslips which contain either cell monolayers or extracellular matrix proteins. After 2 hours, the coverslips are rinsed with medium and examined by fluorescence microscopy and the number of adherent cells are counted. The coverslips contain endothelial cells (positive controls), non-endothelial cells (negative controls) and extracellular matrix proteins (e.g., collagen and fibronectin).

Cells which naturally express SQM2 are used as a positive control; these SQM2+ cells are expected to adhere (in the absence of anti-SQM2 antibodies) to endothelial cells [e.g., SCC-25 (ATCC CRL 1628), HUV-EC-C (ATCC CRL 1730)] and to extracellular matrix proteins (e.g., collagen and fibronectin). The presence of anti-SQM2 antibodies is expected to reduce or abolish the interaction between SQM2+ cells and endothelial cells or extracellular matrix proteins. Cells which do not express SQM2 and which do not receive SQM2 expression vectors are used as negative controls. The ability of anti-SQM2 antibodies to block adhesion of cells containing SQM2 expression vectors to endothelial cells or to extracellular matrix proteins indicates that SQM2 mediates cell adhesion.

VIII. Production of Human SQM2 Specific Antibodies

Human SQM2 substantially purified using polyacrylamide gel electrophoresis (PAGE) (Sambrook, supra) is used to immunize suitable animals (e.g., rabbits, hamsters, rats, mice, goats, sheep, etc.) and to produce antibodies using standard protocols (alternatively, recombinant human SQM2 fusion proteins may be purified by affinity or metal chelation chromatography and used to immunize animals).

The amino acid sequence translated from human SQM2 is analyzed using DNAStar software (DNAStar Inc.) to determine regions of high immunogenicity and a corresponding oligopolypeptide is synthesized and used to raise antibodies by means known to those of skill in the art. Analysis to select appropriate epitopes, such as those near the C-terminus or in hydrophilic regions is described by Ausubel F. M. et al. (supra).

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel F. M. et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

Purified human SQM2 (native or fusion proteins) may be used to generate antibodies which react specifically with the human SQM2 protein. The production of both polyclonal and monoclonal antibodies utilize techniques standard to the art. Polyclonal antibodies contain a mixture of different types of antibodies that are specific for many different antigens present on the immunogen. Monoclonal antibodies contain a single species of antibody having a defined specificity.

Briefly, polyclonal antibodies are generated by immunization of a host animal with a purified protein. The serum of the immunized animal will contain antibodies directed against one or more epitopes of the injected protein. When rabbits are used for the production of polyclonal antibodies specific for human SQM2, 50 to 1000 µg of purified human SQM2 is mixed with complete Freund's adjuvant and administered subcutaneously (s.c.) to the rabbit. Typically, multiple s.c. injections, each containing a maximum volume of about 400 µl are administered (up to 10 injections may be performed per animal). Alternatively, the immunogen may be administered by intramuscular or intradermal injection. Four to six weeks following the initial or primary injection, secondary or booster injections are administered (these may utilize incomplete Freund's adjuvant). Additional boosts are given in 4–6 week intervals following the last injection. Immunized rabbits are bled (e.g., using the marginal ear vein) and the serum is screened for the presence of antibodies which react specifically with human SQM2 (e.g., by ELISA screening).

Immunization of mice is conducted as described above with the exception that the dose of antigen is 10–50 µg per injection (250 µl antigen solution mixed with 250 µl complete Freund's adjuvant) and injection is given intraperitoneally (i.p.). The first boost is given two weeks later and employs incomplete Freund's adjuvant; subsequent boosts are given at about 3 week intervals. Serum is collected from the immunized mice (e.g., by tail bleeding) and is screened for the presence of antibodies which react specifically with human SQM2 (e.g., by ELISA screening).

Monoclonal antibodies are produced by immunizing a host animal with purified human SQM2 protein (native or fusion). Once the host has produced antibodies specific for human SQM2 protein, the spleen of the host is removed. The plasma cells present in the spleen of the immune host are then fused with a myeloma cell (the "fusion partner") to produce hybridoma cells. When mice are immunized for the production of plasma cells to be used to generate hybridomas, suitable fusion partners include the X63Ag8.653, Sp2/0-Ag14, FO, NSI/1-Ag4-1, NSO/I and FOX-NY cell lines [*Antibodies: A Laboratory Manual*, Harlow and Lane, Eds. (1988) Cold Spring Harbor Laboratory Press, Cold Spring Harbor, N.Y., p. 144]. When rats are immunized for the production of plasma cells to be used to generate hybridomas, suitable fusion partners include the YB2/0 and IR983F cell lines (Harlow and Lane, supra). Mice or rats are immunized as described above. Following the generation of specific anti-human SQM2 antibodies in the animals (typically following 2 to 3 booster injection and about 56 days following the initial injection), spleens are removed and splenocytes are fused (e.g., using polyethylene glycol) with the desired fusion partner. The fused cells are diluted in the appropriate selective medium and plated in multiwell culture plates. Each hybridoma cell produces a single type of antibody. Culture supernatant from individual hybridoma cells (removed from the hybridomas about 1 week following plating) is screened using standard techniques to identify those hybridoma cells expressing monoclonal antibodies reactive with human SQM2 (see Harlow and Lane, supra for a review of screening techniques).

When a fusion protein is utilized for the production of antibodies, the resulting antibodies may contain antibodies directed against the fusion partner (e.g., GST). These anti-fusion partner antibodies may be removed from a polyclonal sera by chromatography of the sera on a column containing the fusion partner immobilized to a solid support such as Sepharose beads (Pharmacia). For example, to remove anti-GST antibodies from a polyclonal sera raised against a GST fusion protein, the sera is chromatographed on a resin comprising the GST protein covalently linked to glutathione Sepharose. Anti-fusion partner antibodies may be excluded during the routine screening of hybridomas during the production of monoclonal antibodies.

IX. Purification of Naturally Occurring Human SQM2 Using Specific Antibodies

Naturally occurring or recombinant human SQM2 is substantially purified by immunoaffinity chromatography using antibodies specific for human SQM2. An immunoaffinity column is constructed by covalently coupling human SQM2 antibody to an activated chromatographic resin such as CnBr-activated SEPHAROSE beads (Pharmacia Biotech). After the coupling, the resin is blocked and washed according to the manufacturer's instructions.

Extracts from cells expressing human SQM2 are prepared by methods well known in the art (e.g., disruption of fresh or frozen colon, synovium or breast tissue followed by centrifugation to remove cellular debris). Alternatively, a recombinant human SQM2 fragment containing an appropriate signal sequence may be secreted in useful quantity into the medium in which transfected cells are grown.

A human SQM2-containing preparation is passed over the immunoaffinity column, and the column is washed under conditions that allow the preferential absorbance of human SQM2 (e.g., high ionic strength buffers in the presence of detergent). The column is eluted under conditions that disrupt antibody/human SQM2 binding (e.g., a buffer of pH 2–3 or a high concentration of a chaotrope such as urea or thiocyanate ion), and human SQM2 is collected.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. An isolated polynucleotide sequence encoding a polypeptide comprising the amino acid sequence of SEQ ID NO:1.

2. The polynucleotide sequence of claim 1 comprising the nucleic acid sequence of SEQ ID NO:2.

3. An isolated polynucleotide sequence comprising the complement of the polynucleotide sequence of claim 2.

4. A method for detecting the presence of a polynucleotide sequencer encoding a polypeptide comprising the amino acid sequence of SEQ ID NO:1, the method comprising the steps of:
   a) providing:
      i) a biological sample suspected of containing the polynucleotide sequence; and
      ii) a polynucleotide consisting of the sequence of SEQ ID NO:2; and
   b) combining the biological sample with the polynucleotide consisting of the sequence of SEQ ID NO:2 under conditions such that a hybridization complex is formed between the polynucleotide sequence and the polynucleotide consisting of the sequences of SEQ ID NO:2; and
   c) detecting the hybridization complex.

5. The method of claim 4 wherein the polynucleotide sequence is ribonucleic acid.

6. The method of claim 5 wherein the detected hybridization complex correlates with expression of the polynucleotide of SEQ ID NO:2 in the biological sample.

7. The method of claim 4 wherein the polynucleotide sequence is deoxyribonucleic acid.

8. The method of claim 7, wherein the detecting step occurs in conditions that permit the detection of alterations in the polynucleotide sequence.

9. An antisense molecule comprising the nucleic acid sequence complementary to the polynucleotide sequence of claim 2.

10. A pharmaceutical composition comprising the antisense molecule of claim 9 and a pharmaceutically acceptable excipient.

11. An expression vector containing the polynucleotide sequence of claim 2.

12. A host cell containing the expression vector of claim 11.

* * * * *

UNITED STATES PATENT AND TRADEMARK OFFICE
CERTIFICATE OF CORRECTION

PATENT NO. : 5,843,668
DATED : December 1, 1998
INVENTOR(S) : Hillman et al.

It is certified that error appears in the above-identified patent and that said Letters Patent is hereby corrected as shown below:

Col. 41, line 52, delete "sequencer" and insert --sequence--.

Signed and Sealed this

Eighteenth Day of April, 2000

Attest:

Q. TODD DICKINSON

*Attesting Officer*     *Director of Patents and Trademarks*